(12) United States Patent
Marcucci et al.

(10) Patent No.: US 11,643,659 B2
(45) Date of Patent: May 9, 2023

(54) CONDITIONAL-SIRNAS AND USES THEREOF IN TREATING ACUTE MYELOID LEUKEMIA

(71) Applicants: CITY OF HOPE, Duarte, CA (US); CALIFORNIA INSTITUTE OF TECHNOLOGY, Pasadena, CA (US)

(72) Inventors: Guido Marcucci, Duarte, CA (US); Ya-Huei Kuo, Duarte, CA (US); Si-ping Han, Duarte, CA (US); Lisa Scherer, Duarte, CA (US); William A. Goddard, III, Pasadena, CA (US); John Rossi, Duarte, CA (US)

(73) Assignees: CITY OF HOPE, Duarte, CA (US); CALIFORNIA INSTITUTE OF TECHNOLOGY, Pasadena, CA (US)

(*) Notice: Subject to any disclaimer, the term of this patent is extended or adjusted under 35 U.S.C. 154(b) by 0 days.

(21) Appl. No.: 16/786,793

(22) Filed: Feb. 10, 2020

(65) Prior Publication Data
US 2021/0123060 A1    Apr. 29, 2021

Related U.S. Application Data

(63) Continuation of application No. PCT/US2018/046383, filed on Aug. 10, 2018.

(60) Provisional application No. 62/543,812, filed on Aug. 10, 2017.

(51) Int. Cl.
C12N 15/113    (2010.01)

(52) U.S. Cl.
CPC ...... *C12N 15/1135* (2013.01); *C12N 2310/14* (2013.01); *C12N 2310/3519* (2013.01); *C12N 2320/50* (2013.01)

(58) Field of Classification Search
CPC ............ C12N 2320/50; C12N 15/1135; C12N 2310/3519; C12N 2310/14
See application file for complete search history.

(56) References Cited

U.S. PATENT DOCUMENTS

| | | | |
|---|---|---|---|
| 9,725,715 B2 * | 8/2017 | Han | ................ C12N 15/111 |
| 2011/0195848 A1 | 8/2011 | Roopra et al. | |
| 2012/0088815 A1 | 4/2012 | Liang | |
| 2015/0065555 A1 | 3/2015 | Brown et al. | |
| 2016/0046934 A1 | 2/2016 | Han et al. | |
| 2016/0130581 A1 | 5/2016 | Han et al. | |

OTHER PUBLICATIONS

American Cancer Society, "Key Statistics for Acute Myeloid Leukemia (AML)," Jan. 25, 2017, https://www.cancer.org/cancer/acute-myeloid-leukemia/about/key-statistics.html, accessed Oct. 27, 2020.
Estey, E. H., "Acute Myeloid Leukemia: 2012 Update on Diagnosis, Risk Stratification, and Management," Am. J. Hematol. 87(1):89-99 (2012).

(Continued)

*Primary Examiner* — Terra C Gibbs
(74) *Attorney, Agent, or Firm* — Perkins Coie LLP; Lara J. Dueppen

(57) ABSTRACT

Disclosed herein are conditional siRNAs activatable by CBFβ-MYH11 oncogenic gene and use thereof for treating conditions such as acute myeloid leukemia (AML). The conditional siRNAs target MCL-1 or HDAC8.

16 Claims, 28 Drawing Sheets

Specification includes a Sequence Listing.

(56) References Cited

OTHER PUBLICATIONS

Glaser, S. P., et al., "Anti-apoptotic Mcl-1 is Essential for the Development and Sustained Growth of Acute Myeloid Leukemia," Genes Dev. 26:120-125 (2012).
Kadkol, S. S., et al., "Comprehensive Analysis of CBFbeta-MYH11 Fusion Transcripts in Acute Myeloid Leukemia by RT-PCR Analysis," J. Mol. Diag. 6(1):22-27 (2004).
Landry, B., et al., "Progress in RNAi-Mediated Molecular Therapy of Acute and Chronic Myeloid Leukemia," Mol. Ther. Nucl. Acids 4:e240 (2015).
Look, A. T., et al., "Oncogenic Transcription Factors in the Human Acute Leukemias," Science 278:1059-1064 (1997).
United States Patent and Trademark Office, International Search Report and Written Opinion dated Jan. 4, 2019 for PCT/US18/46383, 13 pages.
Zhang, H., et al., "Mcl-1 is Critical for Survival in a Subgroup of Non-Small-Cell Lung Cancer Cell Lines," Oncogene 30:1963-1968 (2011).

\* cited by examiner

Fig. 6

ABSTRACT

The purpose of this project is to characterize a conditional siRNA designed to treat AML. Specifically the cond-siRNA is designed to target MCL-1 mRNA in Acute Myeloid Leukemia cells when activated with a CBFβ-MYH11 oncogenic transcript. Preliminary testing using dual luciferase assays demonstrated an experimental 15-fold activity difference between the ON and OFF states. However, in the experimental trials testing for activation inside of cells, the cond-siRNA only showed a two-fold activation, after both 48 and 68 hours. The background activation from the OFF constructs was consistently high during experimentation. Further trials will be conducted to determine if more activation is possible with the current cond-siRNA construct, with the goal of creating a novel cond-siRNA therapeutic for AML.

Fig. 9

INTRODUCTION

According to the American Cancer Society, 21,380 new cases of Acute Myeloid Leukemia (AML) were diagnosed in 2017.[1] AML is a fast-moving cancer of the blood, resulting in a build-up of undeveloped white blood cells, known as blasts, and responsible for 10,590 deaths in the past year. This project focused on a subset of AML in which the fusion oncogene CBFβ-MYH11 was present. This chromosomal mutation is found in approximately 12% of AML patients.[2] Using conditional siRNA nanotechnology, an RNA nanostructure was constructed to recognize a specific sequence of the CBFβ-MYH11 gene, and to release an siRNA coding for the knockdown of MCL-1 mRNA. MCL-1 is an anti-apoptotic protein, necessary for the survival of AML cells.[3] Because of the importance of MCL-1 expression for AML cell survival, it is believed that knocking down MCL-1 mRNA in CBFβ-MYH11 AML cells will cause cancer cell death.

Figure 3. (above) sensor strand binding and siRNA activation.

Figure 4. (below) RNA interference pathway showing Dicer processing of siRNA, RISC (RNA Induced Silencing Complex) loading, and final Argonaute complex formation. Photos courtesy of Dr. Han Figure 5. Chromosome 16 inversion that creates the fusion oncogene CBFβ-MYH11.
http://atlasgeneticsoncology.org/Anomalies/inv16p13q22TreatRelID1297.html

Fig. 13

METHODS

Design and purchase Guide (M1), Core (K1), and Sensor (Y3) siRNA strands

Combine and anneal ON M1K1Y3 AML and OFF M1K1Y3 strands

Gel purify and collect constructs 

Purify constructs with electro-dialysis 

Gel quantify constructs 

Design dual luciferase cell experiments for ON/OFF and Activation 

Transfect cells with siRNA constructs 

Perform dual luciferase assay and gather data on mRNA knockdown 

Fig. 14

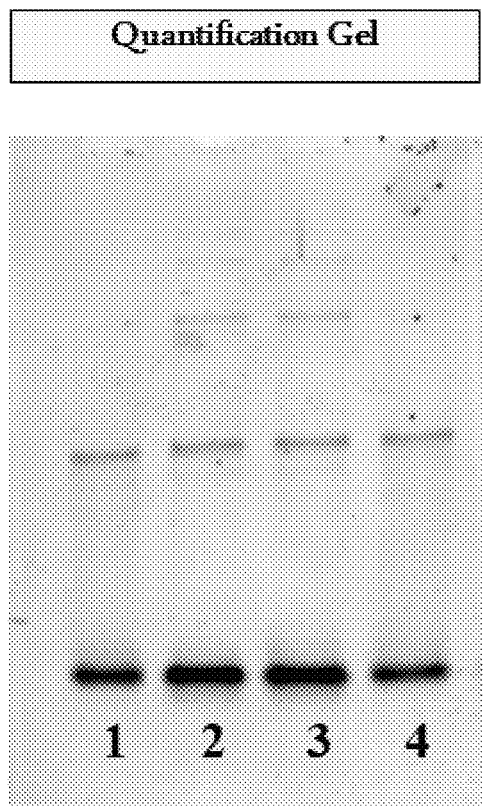

*Figure 6. Quantification of purified cond-siRNA constructs.*

*Lane 1: 100 nm crude cond-siRNA*

*Lane 2: unknown concentration pure cond-siRNA*

*Lane 3: unknown concentration pure cond-siRNA*

*Lane 4: 100 nm crude cond-siRNA*

*The Pure was calculated to be at a concentration of 181.2 nM. The fainter bands seen in the gel are representative of impurities, such as strands that did not anneal in the 4 strand ideal siRNA construct.*

Figure 7. Graph of relative renilla fluorescence readout in a dual luciferase assay. HCT116 cells were treated with the M1K1Y3 OFF and M1K1Y3 AML ON siRNA constructs. The OFF construct shows less MCL-1 knockdown than the ON construct. At 1 nM concentration, the OFF construct knocked down about 82% of renilla, while the ON knocked down about 99%.

Figure 8. Graph of first activation experiment of AML cond-siRNA (48 hr). There is around two-fold activation. The 0.06 nM construct in the irr. activator and the AML activator are lower than expected.

Figure 9. Graph of second activation experiment of AML cond-siRNA (68 hr). Two-fold activation was seen. There is a 14-fold difference between the ON and OFF constructs.

Fig. 18

CONCLUSIONS

The OFF and preactivated ON cond-siRNAs constructs demonstrate a large differential target knockdown (up to ~20 fold at 1 nM) in our assays, providing a broad assay range that facilitates observation of activation.

In these experiments, a consistent two-fold activation was observed at 48 and 68 hours for the 1 nM concentration. Previous studies with similar constructs suggest that activation can be more readily observed by reducing background RNAi activity of the OFF constructs with more stringent purification and extending the time of activation.

Fig. 19

FUTURE DIRECTIONS

In the future, an effort will be made to understand why the OFF construct is actively knocking down the Renilla/MCL-1 transcript inside cells. Experiments will be performed in order to determine whether purification of the cond-siRNA construct needs to be optimized, or whether further design efforts will be needed to stabilize the construct with crosslinking or further base modifications.

Once the OFF construct is dependably OFF, and activation is reliably seen, dual luciferase cell experiments will be conducted with cells that express the endogenous AML fusion gene.

When there are sufficient successful cell trials, the AML siRNA will move on to testing in animal models.

Fig. 20

Leukemic blast death over time after loss of MCL-1 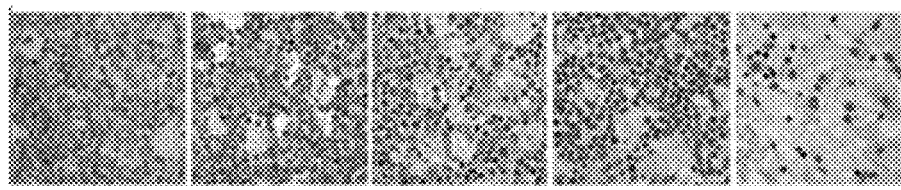

*http://genesdev.cshlp.org/content/26/2/120.full*

Cond-siRNA Activation Trial Knockdown

Graph of cond-siRNA Knockdown of target relative to controls. The most knockdown seen in 48%.

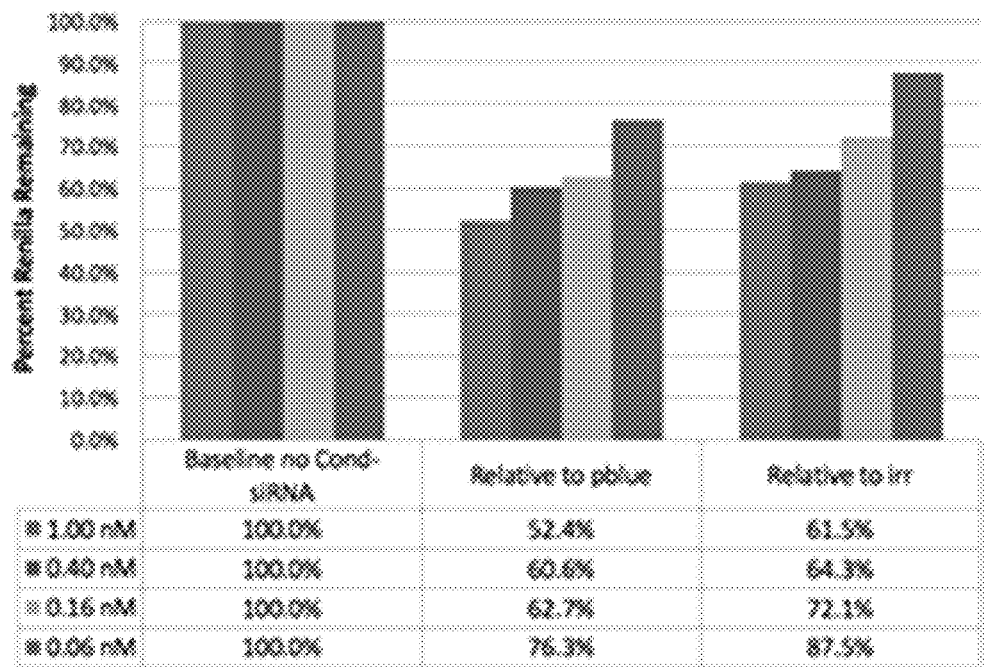

| | Baseline no Cond-siRNA | Relative to pblue | Relative to irr |
|---|---|---|---|
| 1.00 nM | 100.0% | 52.4% | 61.5% |
| 0.40 nM | 100.0% | 60.6% | 64.3% |
| 0.16 nM | 100.0% | 62.7% | 72.1% |
| 0.06 nM | 100.0% | 76.3% | 87.5% |

REFERENCES
1. "What are the key statistics about acute myeloid leukemia" *American Cancer Society*. 5 Jan. 2017, https://www.cancer.org/cancer/acute-myeloid-leukemia/about/key-statistics.html. Accessed 24 July 2017.
2. Look, Thomas A. "Oncogenic Transcription Factors in the Human Acute Leukemias" *Science*, Vol. 278, Issue 5340, pp. 1059-1064
3. Glaser, Stefan P. et al. "Anti-apoptotic Mcl-1 is essential for the development and sustained growth of acute myeloid leukemia" *Genes & Dev.* Vol. 26 pp. 120-125

ACKNOWLEDGEMENTS

Dr. Rossi, Dr. Si-Ping Han, Dr. Lisa Scherer
Marwa BenHajSalah, Robin Hu, Sahil Sagar
Stephanie Patterson, Dr. Kate Sleeth
Sarah Bannister, Tracy Kurry
Eugene and Ruth Roberts Summer Academy
Ford Research Mentor's Endowment
Occidental College Undergraduate Research Center

CONDITIONAL-SIRNAS AND USES THEREOF IN TREATING ACUTE MYELOID LEUKEMIA

PRIORITY CLAIM

This application is a continuation of International Application No. PCT/US2018/046383, filed Aug. 10, 2018, which claims priority to U.S. Provisional Patent Application No. 62/543,812, filed Aug. 10, 2017, the subject matter of which is hereby incorporated by reference in their entirety, as if fully set forth herein.

STATEMENT REGARDING FEDERALLY SPONSORED RESEARCH

This invention was made with government support under Grant Number 1332411, awarded by National Science Foundation through the Emerging Frontiers in Research and Innovation, Origami Design for Integration of Self-assembling Systems for Engineering Innovation (EFRI-ODISSEI), and Grant Number A1029329, awarded by National Institutes of Health (NIH). The government has certain rights to the invention.

SEQUENCE LISTING

This application contains a Sequence Listing, which was submitted in ASCII format via EFS-Web, and is hereby incorporated by reference in its entirety. The ASCII copy, created on Jan. 14, 2021, is named 8175US01_SubstituteSequenceListing.txt and is 8 KB in size.

BACKGROUND

RNA interference (RNAi) is a sequence-specific mRNA degradation pathway mediated by siRNA duplexes, key for cellular immunity and developmental regulation (FIG. 2). Researchers have utilized synthetic RNAi triggers for therapeutics by inhibiting a specific gene product found to be essential in disease driving pathways but non-essential for normal functioning.

Consider however that some genes essential in disease progression may have vital functions in normal cells and are dangerous to target. Meanwhile other upregulated genes are not essential for disease progression, but serve as effective indicators. Therefore, there is a need in the art to develop effective therapies to exploit this differential expression in various indications, such as Acute Myeloid Leukemia (AML).

According to the American Cancer Society, 21,380 new cases of Acute Myeloid Leukemia (AML) were diagnosed in 2017.[1] AML is a fast-moving cancer of the blood, resulting in a build-up of undeveloped white blood cells, known as blasts, and responsible for 10,590 deaths in the past year.

Current molecularly targeted cancer drugs work by inhibiting specific genes that are essential for the survival of cancer cells but non-essential to normal cells. This strategy does not work on all cancers: three recent studies in precision medicine found targetable mutations in 10%[2], 45%[2], or 75% of late stage patients[3]. Even when cancer specific drug targets are present, the heterogeneity of cancer cells in late stage disease often leads to rapid development of drug resistance[4]. Thus, in clinical practice, current approaches have significant limitations and therefore, a more effective treatment is needed. The compositions, constructs, and techniques disclosed herein satisfy this need.

BRIEF DESCRIPTION OF THE DRAWINGS

FIGS. 6-20 show various panels of Appendix A.

DETAILED DESCRIPTION

Overview of Conditional-siRNA

Described herein are conditional siRNA complexes (also referred to herein as Cond-siRNA, a conditional RNA-sensor, or an RNA-sensor) that include a therapeutic component (e.g., siRNA molecule) associated with a molecular sensor via a core molecule. The conditional siRNA complexes are inactive under normal conditions, but are activated upon interaction between the molecular sensor and a biomarker. Such molecules are synthetic riboswitch molecules that allow an input gene or RNA molecule to "switch on" an RNAi pathway against a target output gene.

Figure 21:
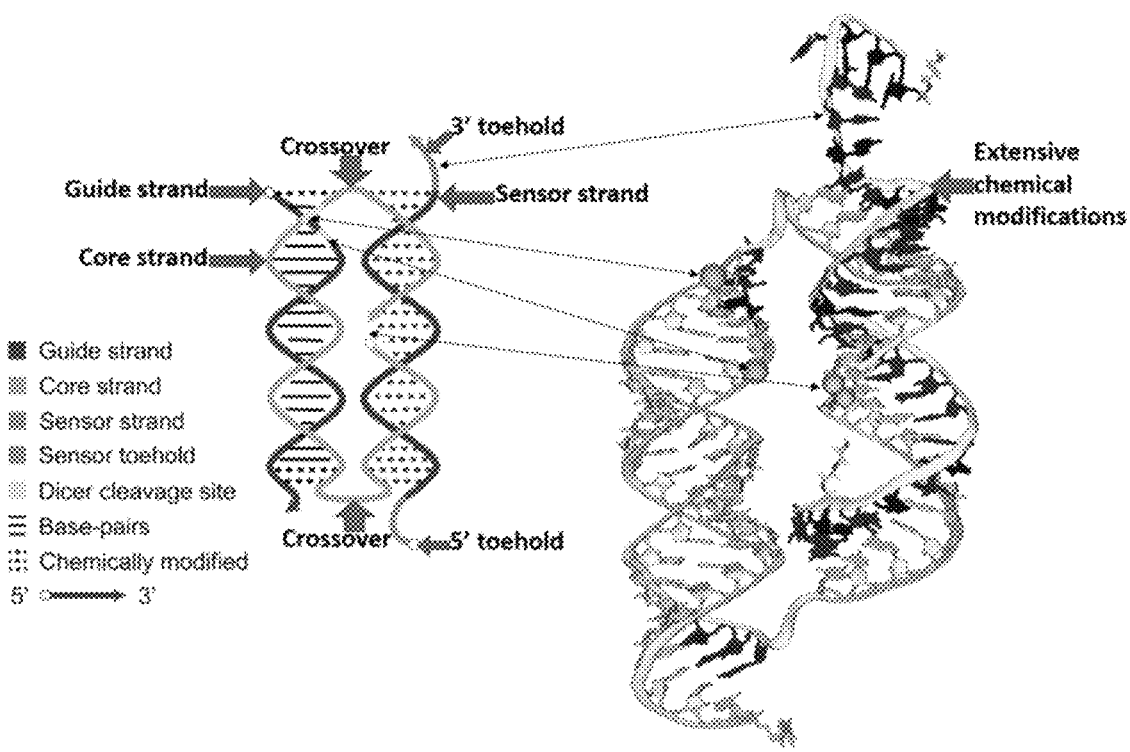
FIG. 21 shows a comparison of secondary and tertiary structure (from full atomistic MD simulations) of a Cond-siRNA construct according to one embodiment. Black arrows show corresponding features between the 2D and 3D representations.
Figure 22:
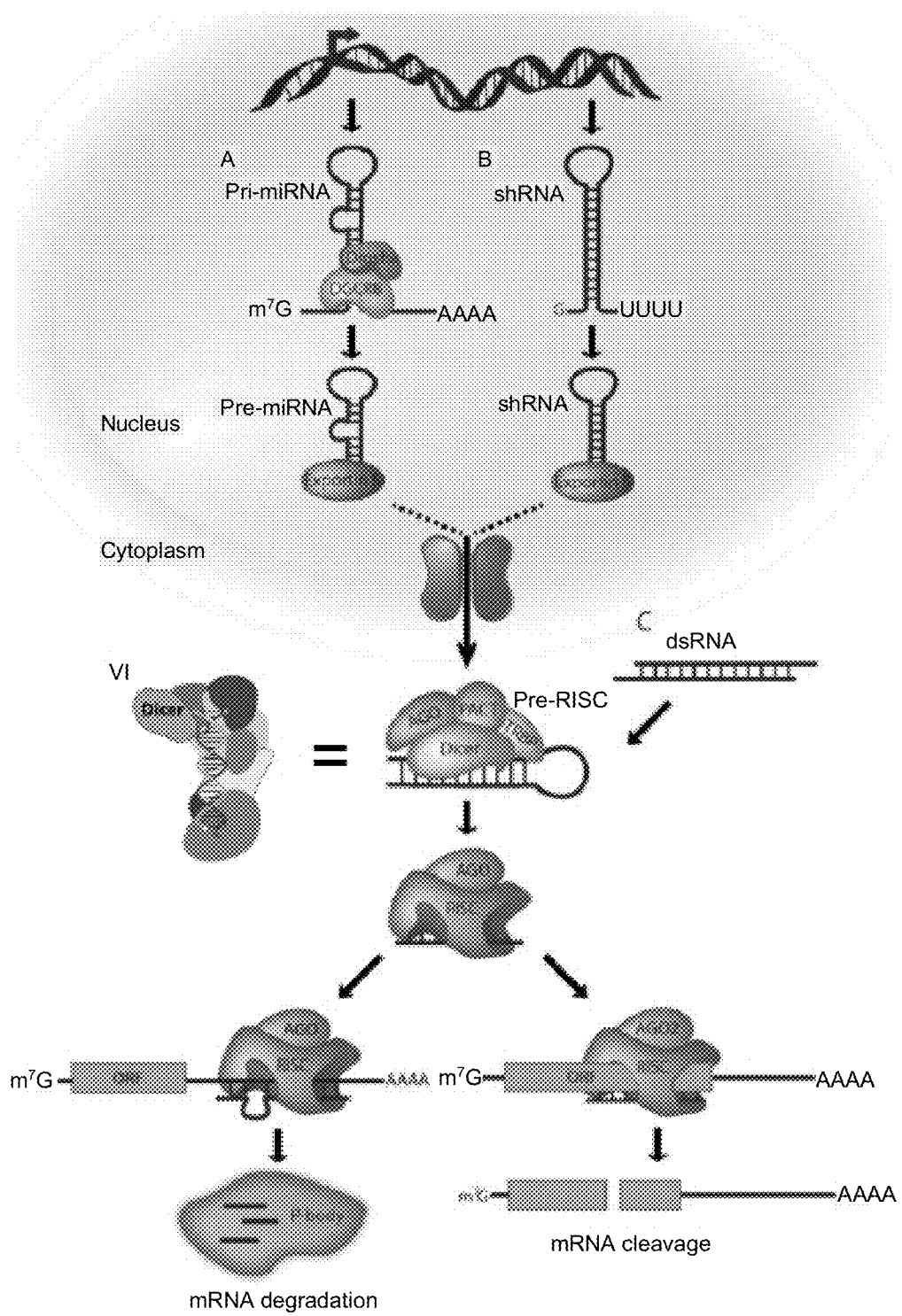
FIG. 22 is a diagram showing the RNAi pathway.

An RNA-sensor molecule or complex includes sensor strand, a guide strand, and a core strand that bind to each other to form a multi-strand molecular complex having a dual duplex structure shown in FIG. 21. In certain embodiments, those three strands (core, sensor and guide) form two parallel oligonucleotide duplexes connected in a double crossover configuration. [14] (See FIG. 21). In some aspects, the length of each of the oligonucleotide duplexes is sufficient to operate within the RNA interference (RNAi) pathway (See FIG. 22). For example, the duplexes may be between about 15 and 30 base pairs in length. In some embodiments, the duplexes are between 15 and 20 base pairs in length, between 20 and 25 base pairs in length, between 25 and 30 base pairs in length. In other embodiments, the duplexes are about 15, 16, 17, 18, 19, 20, 21, 22, 23, 24, 25, 25, 26, 27, 28, 29, 30, or more than 30 base pairs in length.

The double crossover configuration as shown in FIG. 21 represents the inactive or "OFF" state of the RNA-sensor complex wherein the sensor duplex inhibits RNAi loading of the siRNA duplex, serving as a "lock" on RNAi activity. In the OFF state, the guide strand binds a first portion (or "passenger" segment) of the core strand to form an siRNA duplex that serves as a pro-RNA molecule. The pro-RNA molecule operates in the RNAi pathway of a target cell to alter expression of a target gene or target RNA molecule associated with a pathological condition (i.e., the "therapeutic target molecule"). The second duplex is formed by the sensor strand binding to a second portion (or "protection" segment) of the core strand to form the sensor duplex. In some embodiments, the core strand has a third portion (or "protection" segment) that binds the sensor strand. In certain such embodiments, the core strand includes the passenger strand (P) that is joined to first and second protection segments (A, B) at each end by a linker (L1, L2) in the following configuration:

5'B-L2-P-L1-A3'.

The sequence of the core strand is determined by the sequences of the sensor and guide strands, and may be fully or complementary to the sensor strand, the guide strand, or both. Any suitable linker can be used in accordance with the embodiments described herein, including, but not limited to, an internal C3 spacer, a C6 linker, a tri-ethylene glycol linker.

The RNA-sensor complex is activated to the "ON" state upon interaction with a biomarker in the cell expressing a phenotype associated with the pathological condition targeted by the guide strand of the siRNA duplex. This activation is primarily due to the design of the sensor strand, which serves as the activation signal for RNAi activity. When this is the case, the RNA-sensor complex is said to detect the biomarker.

Figure 23:
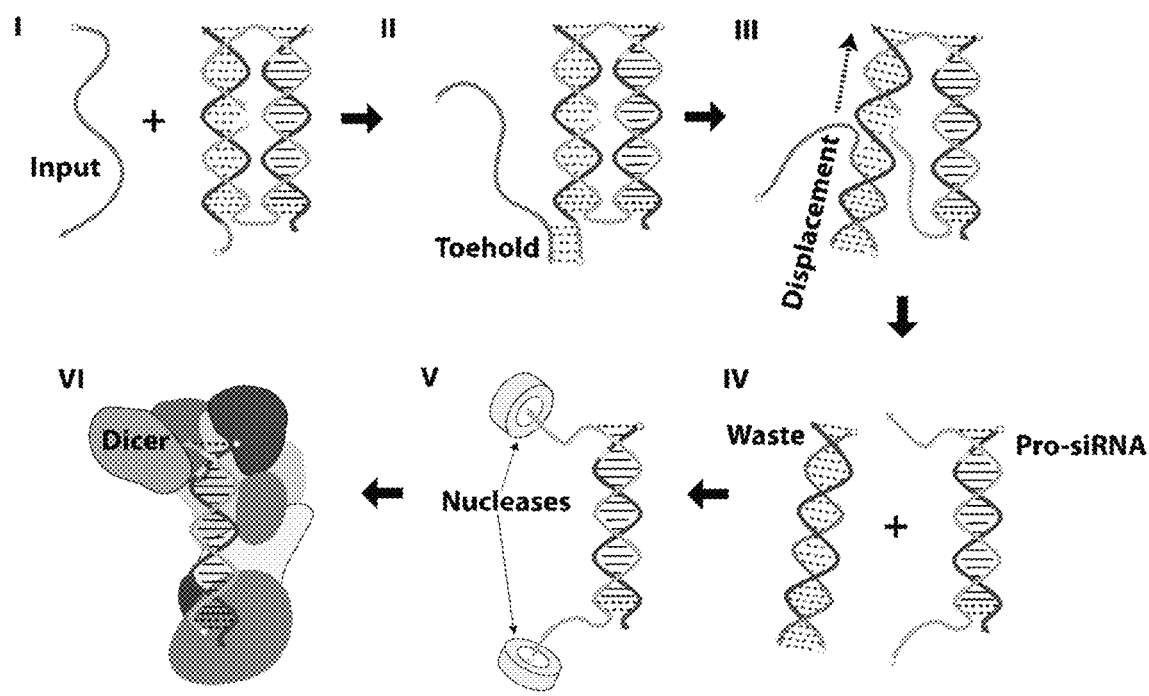
FIG. 23 shows toehold mediated strand displacement process of conditional siRNA. In step I, c-siRNA meets RNA transcript with correct activation sequence (Input). In step II, an Input RNA binds to the toehold. Step III shows toehold mediated strand displacement. Step IV shows the sensor strand and input forming a waste duplex that separates from the pro-siRNA. In step V, XRN1, exosome and other cytosolic RNAses rapidly degrade unprotected overhangs, turning pro-siRNA into efficient Dicer substrate. In step VI, siRNA is processed by Dicer for incorporation into RISC. The basic biophysical process of toehold mediated strand displacement includes a fast 1D random walk: uS to mS for each of N^2 steps. This results in sequence specificity from both toehold and duplexes. Thermodynamically stable chemical modifications are confined to sensor strand to avoid kinetic traps.

The sensor strand includes a nucleotide sequence designed to bind the biomarker associated with the pathological condition (i.e., "pathological biomarker"). Binding to the biomarker is initiated by the binding of at least one toehold segment (single stranded) to an input RNA strand that encodes at least a portion of the pathological biomarker, as shown in FIG. 23. Upon displacement of the sensor strand, the sensor and input strands from a waste duplex that separates from the pro-siRNA molecule, allowing the pro-siRNA to be processed by the target cell's RNAi system. The structure and binding dynamics of the conditional-siRNAs described herein is explained further in U.S. Pat. No. 9,725, 715, the content of which is incorporated herein by reference in its entirety.

The sequence of the sensor strand can be fully or partially complementary to an RNA sequence present in the pathological biomarker. In certain embodiments, the sensor strand is 100% complementary to the RNA sequence present in the pathological biomarker. Other embodiments may include a sensor strand that is largely complementary to the RNA sequence present in the pathological biomarker, for example, the sensor strand may be greater than 70% complementary, greater than 75% complementary, greater than 80% complementary, greater than 85% complementary, greater than 90% complementary, greater than 95% complementary, greater than 96% complementary, greater than 97% complementary, greater than 98% complementary, or greater than 99% complementary to the RNA sequence present in the pathological biomarker.

In some embodiments, the pathological biomarker is an RNA sequence that forms or encodes a molecule that is associated with the pathologic condition. In some aspects, the pathological biomarker is an RNA sequence that is present in the target cell under pathological conditions, but is substantially absent under normal conditions. Alternatively, the pathological biomarker is an RNA sequence that is upregulated in the target cell under pathological conditions as compared to normal conditions.

The guide strand includes a Dicer cleavage site near the 3' end. The sequence between the Dicer cleavage site and the 3' terminus of the guide strand is either fully or partially complementary to a nucleotide sequence found in the therapeutic target molecule (e.g., target gene, target mRNA or target miRNA). When this is the case, the Cond-siRNA is said to target the gene or RNA molecule. In certain embodiments, the guide strand is 100% complementary to the nucleotide sequence found in the therapeutic target molecule. Other embodiments may include a guide strand that is largely complementary to the nucleotide sequence found in the therapeutic target molecule, for example, the guide strand may be greater than 70% complementary, greater than 75% complementary, greater than 80% complementary, greater than 85% complementary, greater than 90% complementary, greater than 95% complementary, greater than 96% complementary, greater than 97% complementary, greater than 98% complementary, or greater than 99% complementary to the nucleotide sequence found in the therapeutic target molecule.

A challenge of using oligonucleotides in vivo lies in preventing nuclease degradation of RNA nucleotides. Several chemical modifications in the sensor strand can be used to overcome this challenge. For example, Locked Nucleic Acids (LNAs) include a modification of RNA nucleotides with an extra bridge between the 2' 0 and 4' C increases thermal stability of RNA duplexes and allows for resistance to nucleases. 2' 0-Methyl modifications confer stability, increase binding affinity to RNA nucleotides and prevent degradation by nucleases. And, phosphorothioate: modification by replacing one of the non-bridging oxygens in the phosphate linkage between bases with a sulfur that reduces nucleolytic degradation; however also lowers binding affinity.

Thus, in certain embodiments, the RNA-sensor complex includes one or more modifications to the nucleotide sequence of the sensor strand, the core strand, and/or the guide strand. Exemplary modifications that may be used include, but are not limited to, locked nucleic acids (LNA), peptide nucleic acids (PNA), 2'-O-methyl modifications, morpholino modifications, phosphorothioate modifications, terminal modifications, and other linker or backbone modifications or connections. Additional chemical modifications may be chosen according to methods described in U.S. Pat. No. 9,725,715B2, the disclosure of which is hereby fully incorporated herein.

Figure 24A:
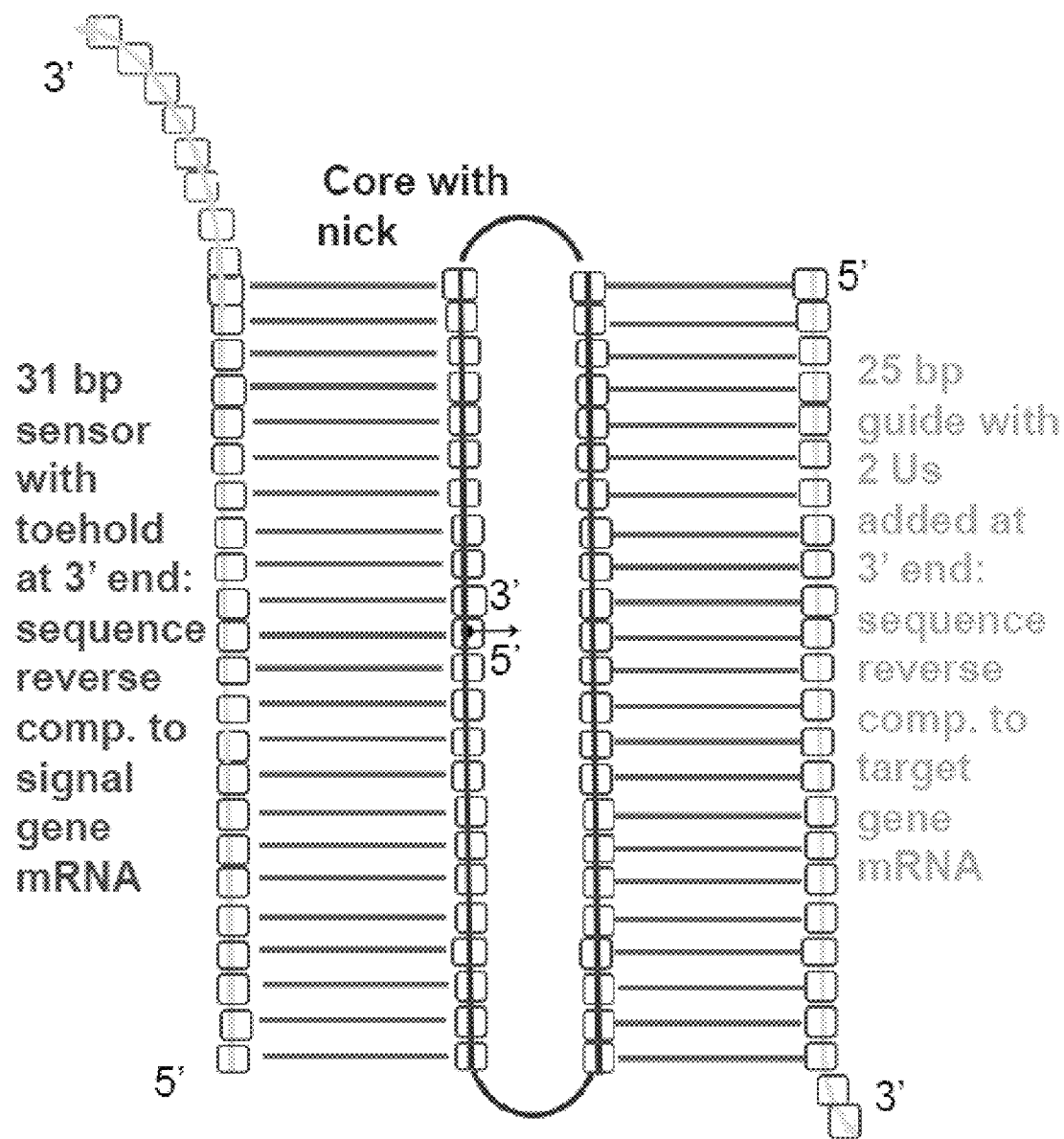
FIGS. 24A-C: A) General construct design of cond-siRNA with green sensor strand designed reverse comp. to signal gene mRNA, red core strand with nick either 11 or 12 bp from toehold end on sensor side designed comp. to sensor and guide, and yellow guide strand designed reverse comp. to target gene mRNA. B) Model of cond-siRNA. C) Molecular simulation of cond-siRNA.
Figure 24B:
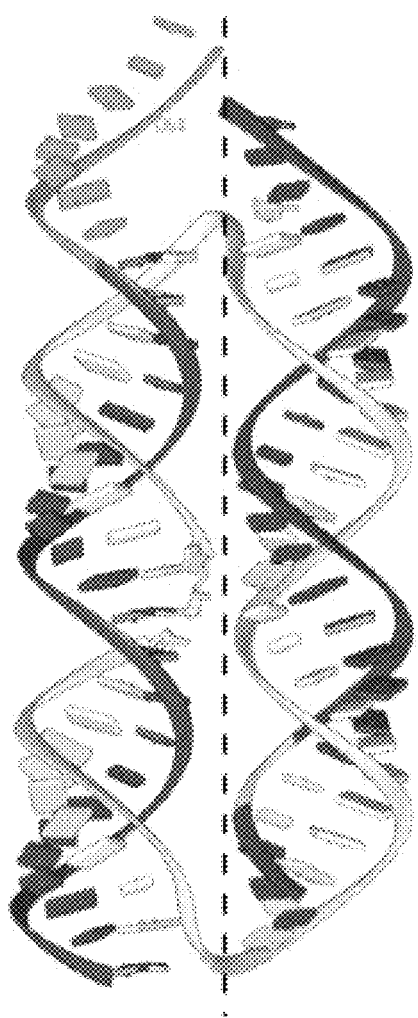
Figure 24C:
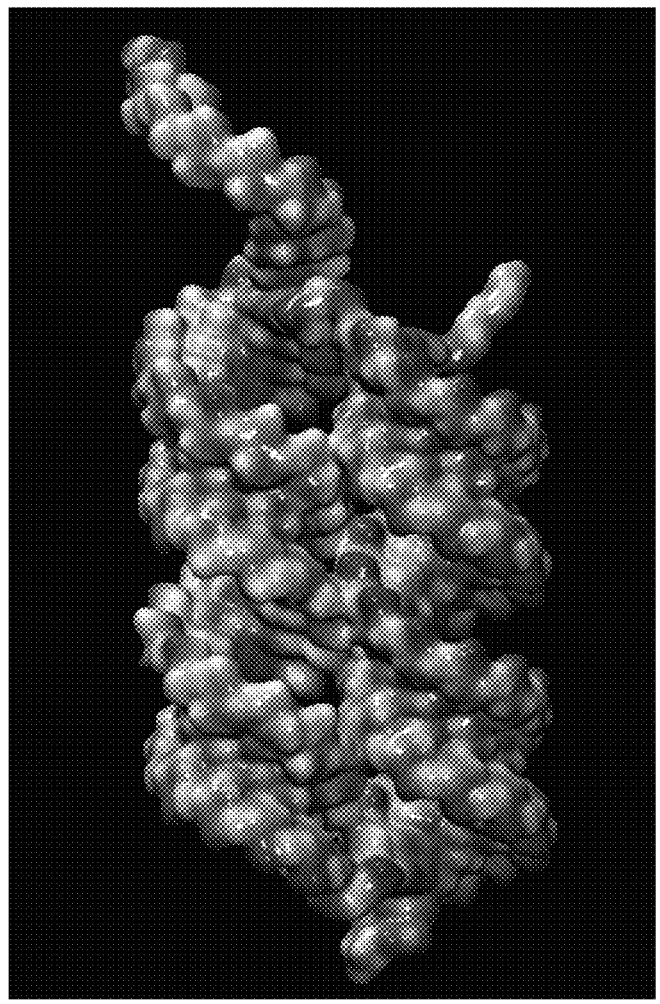

The approach of designing a cond-siRNA sensor complex for use in treating a disease or other pathological condition using the cond-siRNA sensor complexes is advantageous in that it allows the complex to become biologically active only in diseased cells AND remain OFF in healthy cells. In addition, the approach allows for increased disease cell specificity and prevents toxicity from delivery to unintended off-targets. Further, the approach combines disease specificity from one gene with treatment efficacy from a second gene to create therapeutics that are precisely tailored to specific gene expression patterns. Still further, the approach is advantageous due to steric hindrance of the two RNA duplexes positioned in a parallel configuration (FIG. 24). The sensor strand inhibits RNAi loading of siRNA and will only displace when activated in disease cells.

Overview of Methods for Designing a Conditional siRNA Complex

An siRNA complex is designed based on biomarkers and therapeutic target molecules that are specific to each cell type, pathological condition, and/or indication. According to certain embodiments, methods for designing and testing each conditional siRNA complex includes several steps, as described below.

Figure 25:
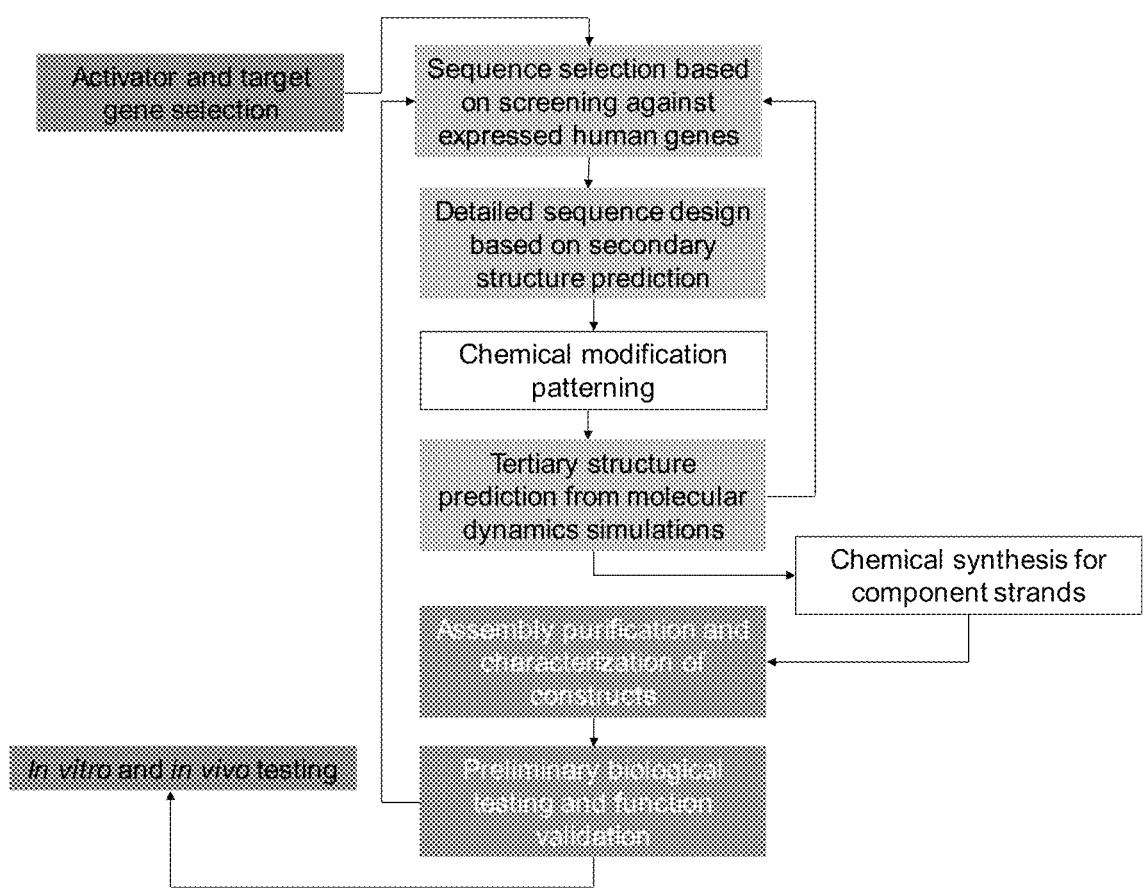
FIG. 25 shows an overview of the design process for Cond-siRNAs according to one embodiment.
Figure 26:
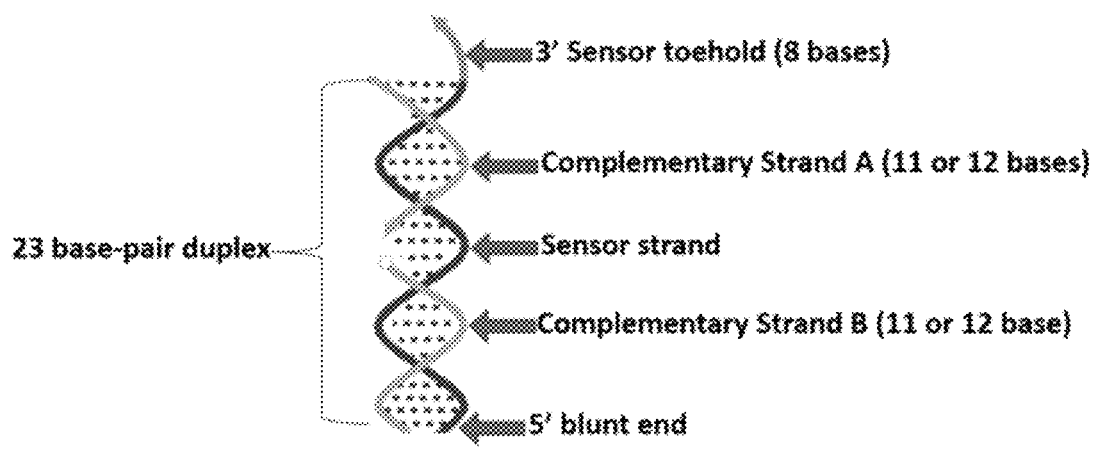
FIG. 26 shows a hypothetical sensor duplex for mRNA used to check for thermodynamic stability of the sensor according to one embodiment.
Figure 27:
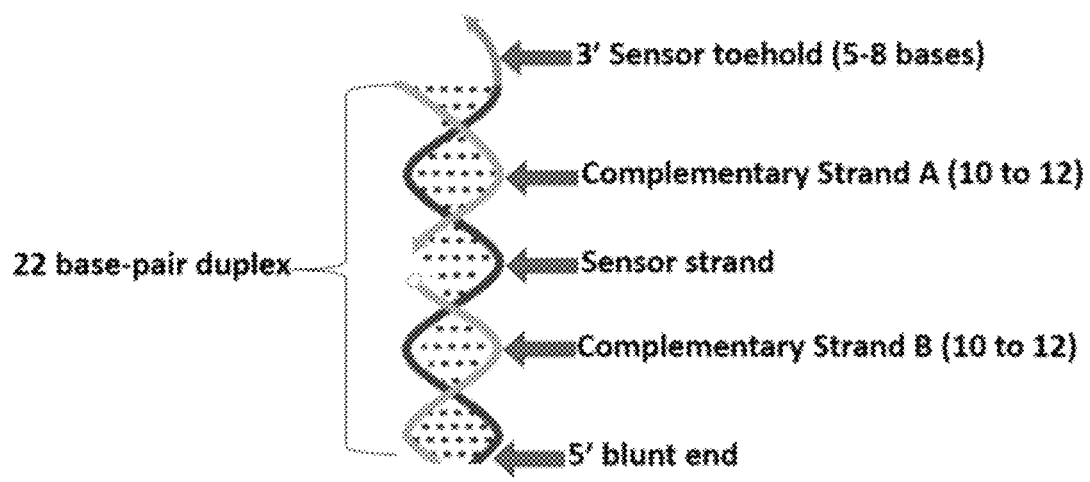
FIG. 27 illustrates a cond-siRNA construct disclosed herein.

FIG. 25 shows an overview of the design process. In certain embodiments methods for designing a conditional siRNA complex (the "design method") includes a step of determining a biomarker that will serve as an input for activation and a therapeutic target for RNAi inhibition. This step may include a determining one or more factors that are differentially expressed (i.e., upregulated or present in a diseased cell as compared to a normal cell) using methods known in the art.

The design method further includes a step of generating a list of candidate target segments of the biomarker (i.e., target mRNA sequence or target miRNA sequence) that can serve as a biomarker segment for binding the sensor strand, and then designing sensor strands for each biomarker.

The design method further includes a step of estimating the thermodynamic stability of the resulting sensor strand-biomarker duplexes (the sensor duplex) generated by the target segments and sensor strands by using secondary structure prediction tools used in the art [15].

The design method further includes a step of checking for the uniqueness of the binding site for the most stable sensor duplexes against the known transcriptome of the animal to which the conditional siRNA complex will be tested against.

The design method further includes a step of generating a list of guide strand sequences by using a protocol that may include, but is not limited to, standard siRNA design tools, literature references, or heuristic rules.

The design method further includes a step of creating a Dicer substrate from the chosen guide strand sequences.

The design method further includes a step of generating sequences for the core strand that connect the sensor strands to the guide strands.

The design method further includes a step of checking that the sensor: guide pairing does not create unwanted interactions.

The design method further includes a step of selecting a pattern of suitable chemical modifications as described herein, and optionally simulating the constructs using molecular simulation methods used in the art [16] to simulate the constructs (optional).

The design method may also include a method of synthesizing or purchasing the sensor, core, and guide strands from commercial vendors such as Qiagen, Dharmacon, or IDT, the constructs of which are then assembled, characterized, and purified using gel electrophoresis.

The design method further includes a step of conducting preliminary biological testing and validation of the construct function, and then optionally test in in vitro and in vivo models of pathological conditions, including, but not limited to, MI induced maladaptive hypertrophy as described below.

Additional embodiments related to designing the guide, the sensor and the core strands are explained below.

Method for Designing Sensor Strands for mRNA Biomarker

According to certain embodiments, methods for designing and testing sensor strands that target an mRNA biomarker includes an algorithm that includes several steps, as described below.

In certain embodiments, a method for designing a sensor strand for an mRNA biomarker (the "mRNA sensor design method") includes a step of identifying the 3' UTR for each messenger RNA biomarker.

The mRNA sensor design method further includes a step of generating all possible consecutive 31 base sequences for each 3' UTR identified above.

The mRNA sensor design method further includes a step of obtaining the prospective sensor strand sequence for each sequence segment from the previous step by identifying the reverse complement (full or partial) of each sequence.

The mRNA sensor design method further includes a step of checking each sensor strand sequence for the following undesirable features: (i) three or more consecutive Gs, and (ii) four or more consecutive A or U bases.

The mRNA sensor design method further includes a step of checking each sensor strand sequence for the following desirable features: (i) higher than 50% G/C bases—this correlates with thermodynamic stability, (ii) "three letteredness," (iii) The first base at the 5' end of the sensor strand is a C or a G; and (iv) the 9th base from the 3' end of the sensor strand is a C or a G. According to the embodiments described herein, "three letteredness" is defined as the proportion of the sequence comprising of the three most numerous bases (e.g., the extent to which sequence is mostly made of A, U, C; or C, G, A; or A, U, G). A higher three letteredness score correlates with lower internal secondary structure.

The mRNA sensor design method further includes a step of ranking all possible sensor strands. Strands with the least number of features from 4 and the highest scores from 5 are ranked highest.

The mRNA sensor design method further includes a step of generating hypothetical sensor duplexes using the pattern, starting from the highest ranked strands.

The RNA sensor design method further includes a step of using Nupack or similar secondary structure prediction codes to calculate the following, starting from the highest ranked strands: (i) the internal secondary structure of the sensor strand (lower amounts of internal secondary structure are desirable, (ii) the thermodynamic stability of the hypothetical duplex from 7. Ideally, at 1 nM strand concentration, Nupack should predict that >90% or >95% of component strands should form the hypothetical sensor duplex; and (iii) if sensor duplex is not stable, can adjust 1 to 5 bases at the 5' terminus of the sensor sequence to increase stability at the cost of reducing complementarity to the corresponding binding site on the putative biomarker.

The RNA sensor design method further includes a step of screening the sensor strand for thermodynamically stable duplexes using NCBI BLAST according to the following parameters: (i) use the "somewhat similar" search option, (ii) for sensor sequences, the 8 bases at the 3' terminus (constituting the 3' toehold) should have no more than 5 bases complementary to known transcripts in the target animal (eg, human or mouse) other than the intended biomarker, and (iii) if the first two criteria not met, broaden sequences considered in 1 to the coding region or the entirety of the mRNA.

Method for Designing Sensors for miRNA Biomarker

According to certain embodiments, methods for designing and testing sensor strands that target an miRNA biomarker includes an algorithm that includes several steps, as described below.

In certain embodiments, a method for designing a sensor strand for an miRNA biomarker (the "miRNA sensor design method") includes a step of identifying a guide sequence for each miRNA biomarker, to which the sensor strand is designed to bind (typically approximately 21 bases according to one aspect).

The miRNA sensor design method further includes a step of obtaining the reverse complement (full or partial) of the miRNA guide sequence.

The miRNA sensor design method further includes a step of adding 8 more bases to the 5' end of the sequence from the prior step.

The miRNA sensor design method further includes a step of generating hypothetical sensor duplexes, starting from the sequence developed in the prior step.

The miRNA sensor design method further includes a step of using Nupack or similar secondary structure prediction codes to calculate the following: (i) the thermodynamic stability of the hypothetical duplex from the prior step. Ideally, at 1 nM strand concentration, Nupack should predict that >90% or >95% of component strands should form the hypothetical sensor duplex. (ii) if sensor duplex is not stable or the secondary structure is incorrect, determine whether the 8 terminal bases at the 5' end of the sensor strand, or the length of strand A or strand B can be altered or modified to optimize thermodynamic stability.

The miRNA sensor design method further includes a step of screening the sensor strand for thermodynamically stable duplexes in NCBI BLAST according to the following parameters: (i) use the "somewhat similar" search option, (ii) for sensor sequences, the 8 bases added at the 5' end of the sensor should not increase complementarity to transcripts other than the intended miRNA. If they do, adjust the sequence and start over from 4.

Methods for Designing a Guide Strand Sequence Against a Therapeutic Target Molecule According to certain embodiments, methods for designing a guide strand sequence against a therapeutic target gene or RNA molecule (e.g., mRNA or miRNA) includes several steps, as described below.

In certain embodiments, a method for designing a guide strand sequence against a therapeutic target (the "guide strand design method") includes a step of obtaining one or more prospective guide strand sequences using at least one of the following methods: (i) find a published guide strand sequence for the intended target; (ii) find a known miRNA target site on the target gene, or (iii) use a published algorithm or design tool known in the art [17,18].

The guide strand design method further includes a step of checking the guide sequence to make sure that the 6 bases at the 5' domain is more AU rich than the 6 bases in the 3' domain. This will improve probability for correct strand loading [19]. Ideally, the 3' domain should be CG rich, and terminate in a CG base-pair.

The guide strand design method further includes a step of adding four terminal bases to the 5' end of the guide strand to complete the duplex. Those should be CG rich to improve thermodynamic stability.

The guide strand design method further includes a step of constructing the hypothetical RNAi targeting duplex.

The guide strand design method further includes a step of checking that the guide strand has weak internal secondary structure and minimal tendency to bind to itself (no more than 10% at 1 nM strand concentration) using Nupack or similar standard secondary structure calculation tool. Adjust bases added in 3 as necessary.

Methods for Designing a Core Strand Sequence and Checking Compatibility of Pairing Sensor to Guide According to certain embodiments, methods for designing a core strand sequence and checking compatibility of pairing sensor to guide includes several steps, as described below.

In certain embodiments, a method for designing a guide strand sequence against a therapeutic target (the "core strand design method") includes a step of choosing a suitable combination of sensor and guide strands, methods for designing those strands are discussed above and in the working examples, according to the embodiments described herein.

Figure 10:
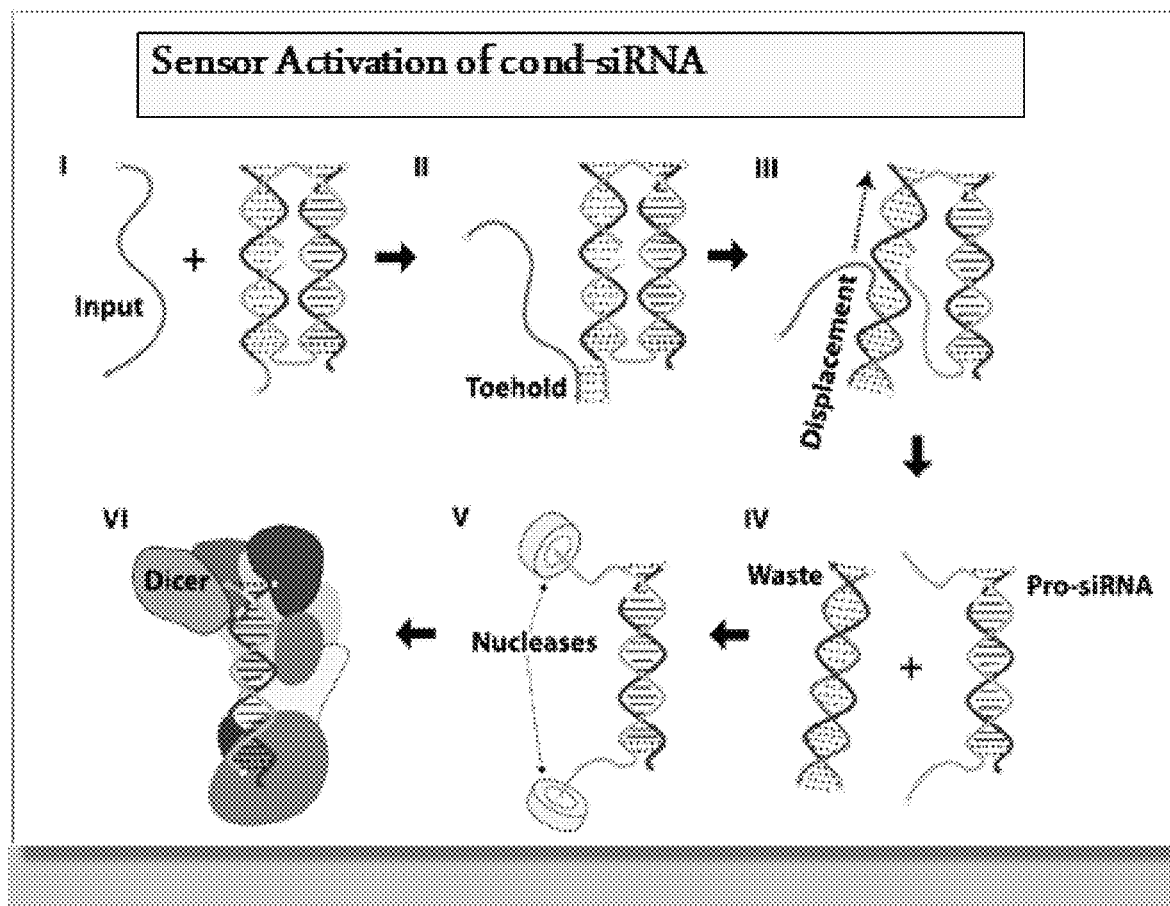
Figure 11:
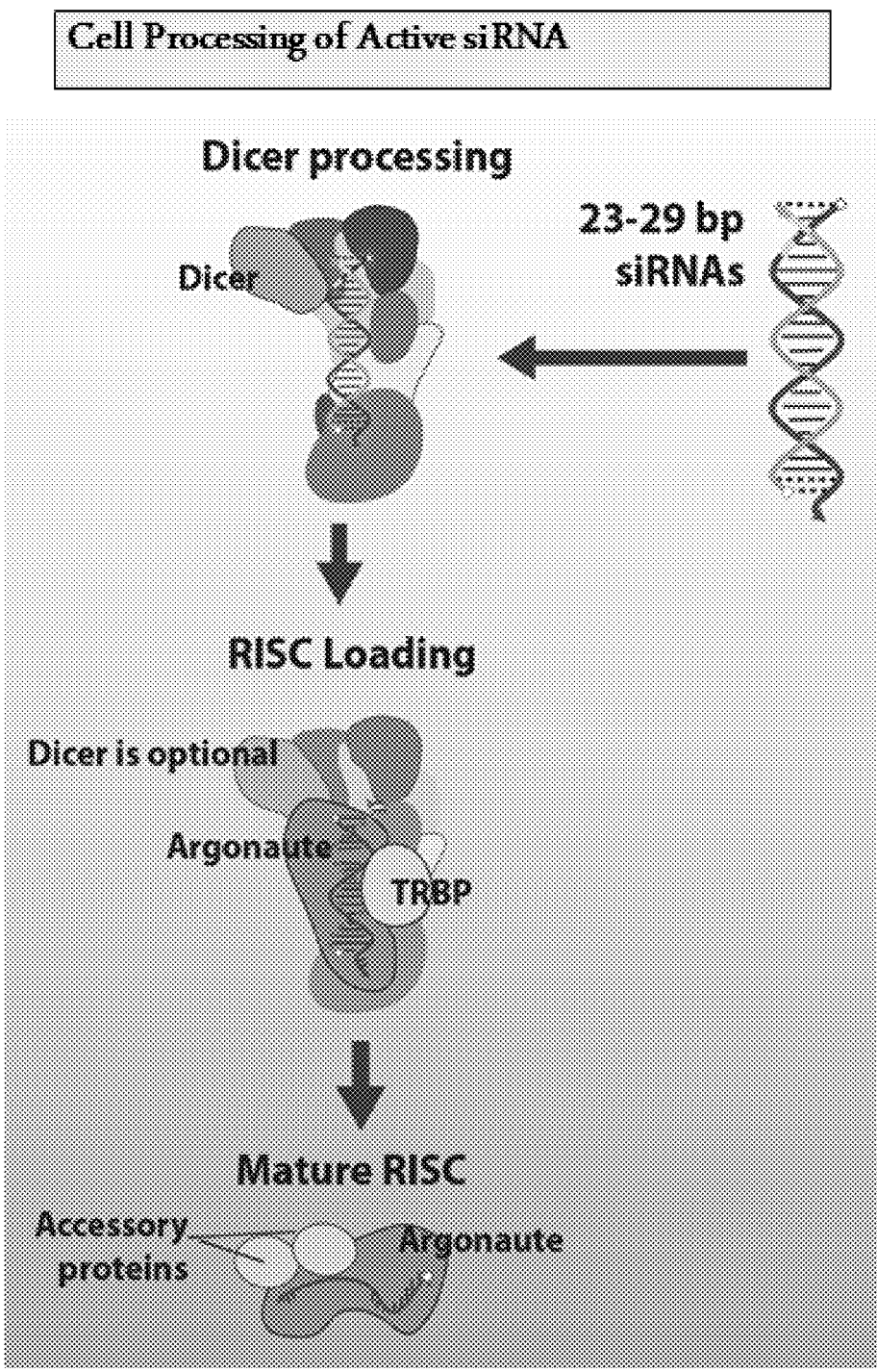
Figure 12:
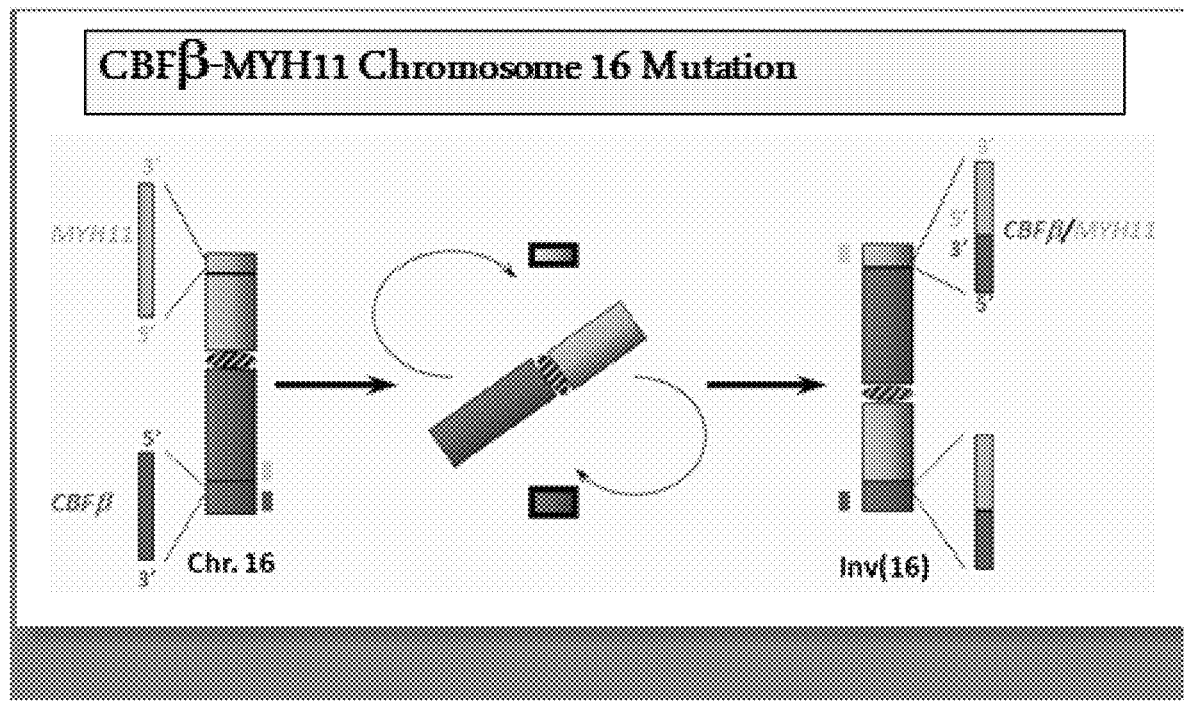
Figure 15:
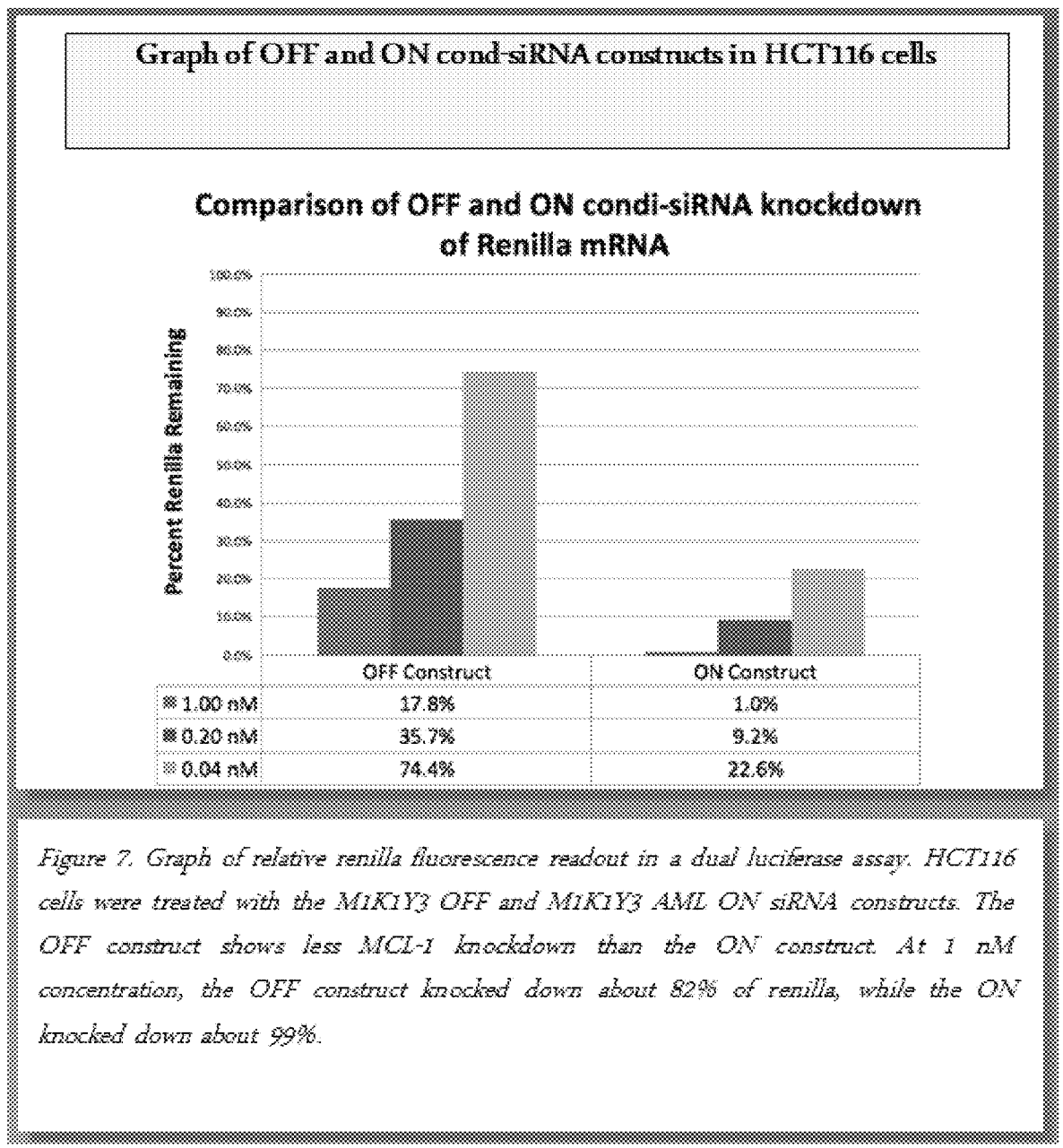
Figure 16:
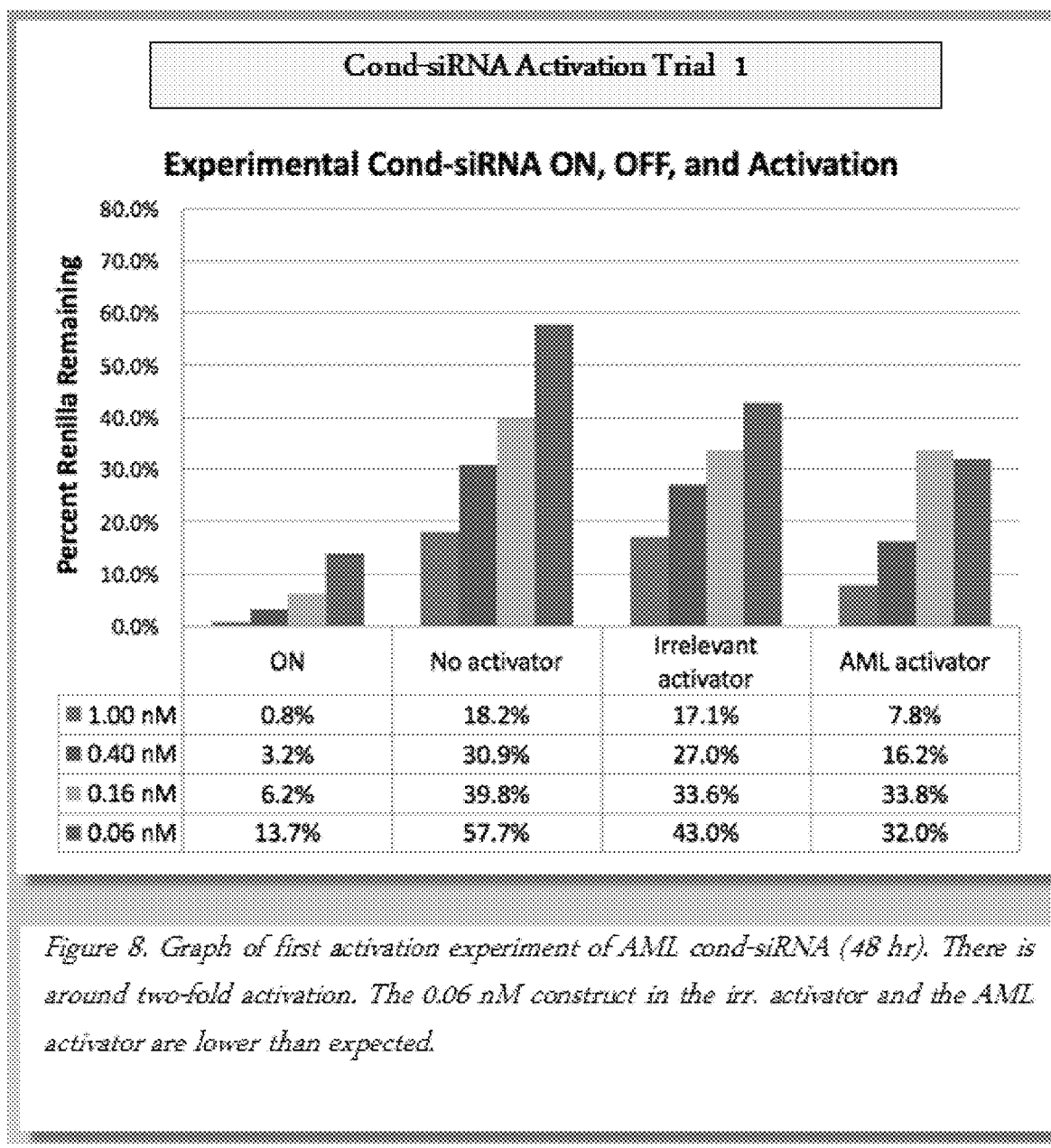
Figure 17:
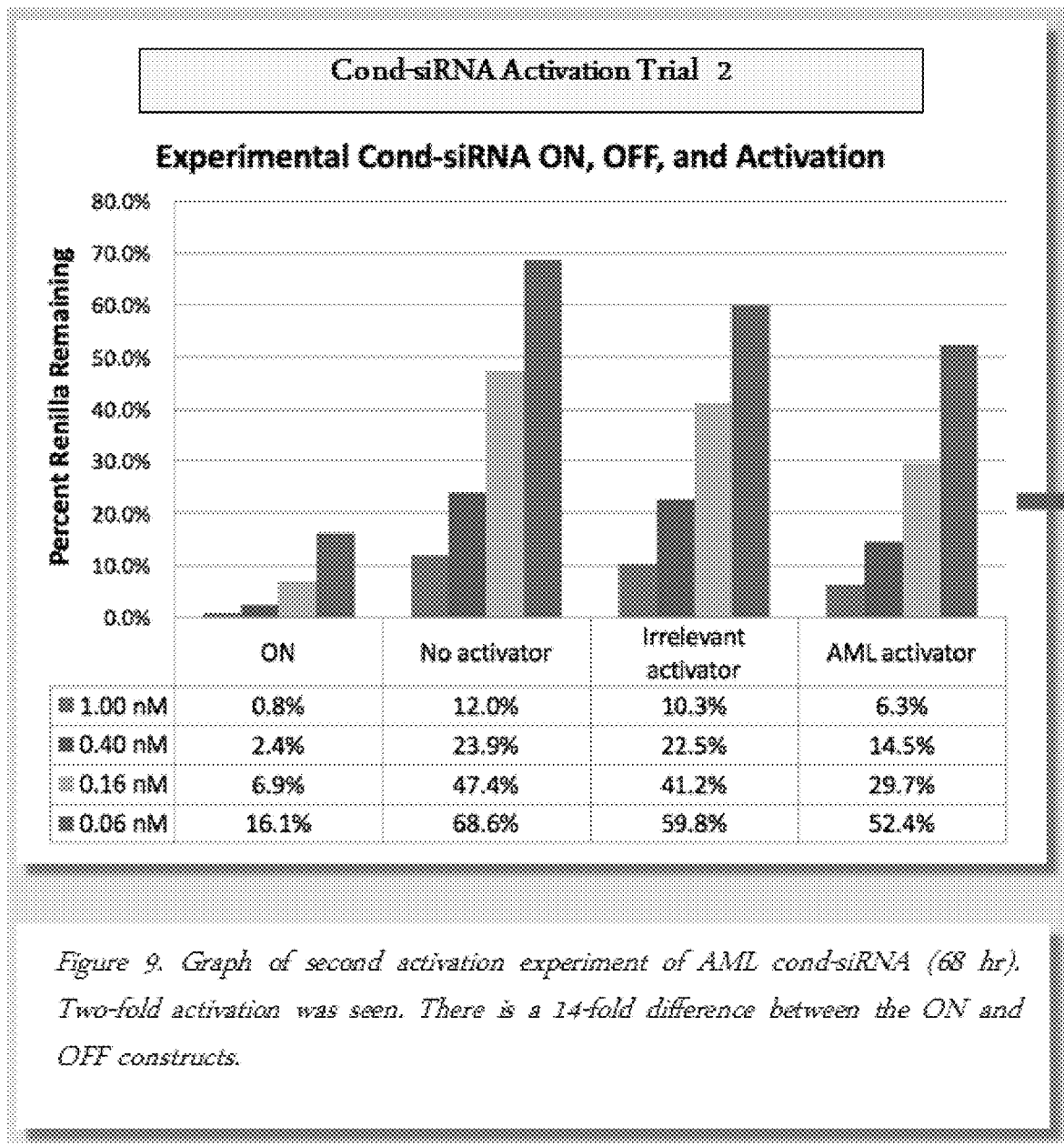

The core strand design method further includes a step of constructing the core strand by constructing a strand of the form 5'-B-C3-P-C3 A-3' where A and B are the sequence of complementary strand B from the hypothetical sensor duplex (FIG. 6 or 9), P is the sequence of the passenger strand from the hypothetical RNAi duplex (FIG. 10) and C3 are C3 linkers.

The core strand design method further includes a step of using Nupack or similar standard secondary structure calculation tool to check that the guide strand and core strand base-pairing has the following properties: (i) >95% of strands are base-paired in the correct duplex at 1 nM strand concentration, (ii) the guide strand duplex has the correct conformation, with a ~23 base-pair duplex, a two base 3' guide strand overhang, and 10-12 base 5' and 3' core overhangs with minimal secondary structures, and (iii) If above criteria not met, choose new sensor or guide pairing.

Conditional siRNA Complexes for Treating Acute Myeloid Leukemia (AML)

Figure 1:
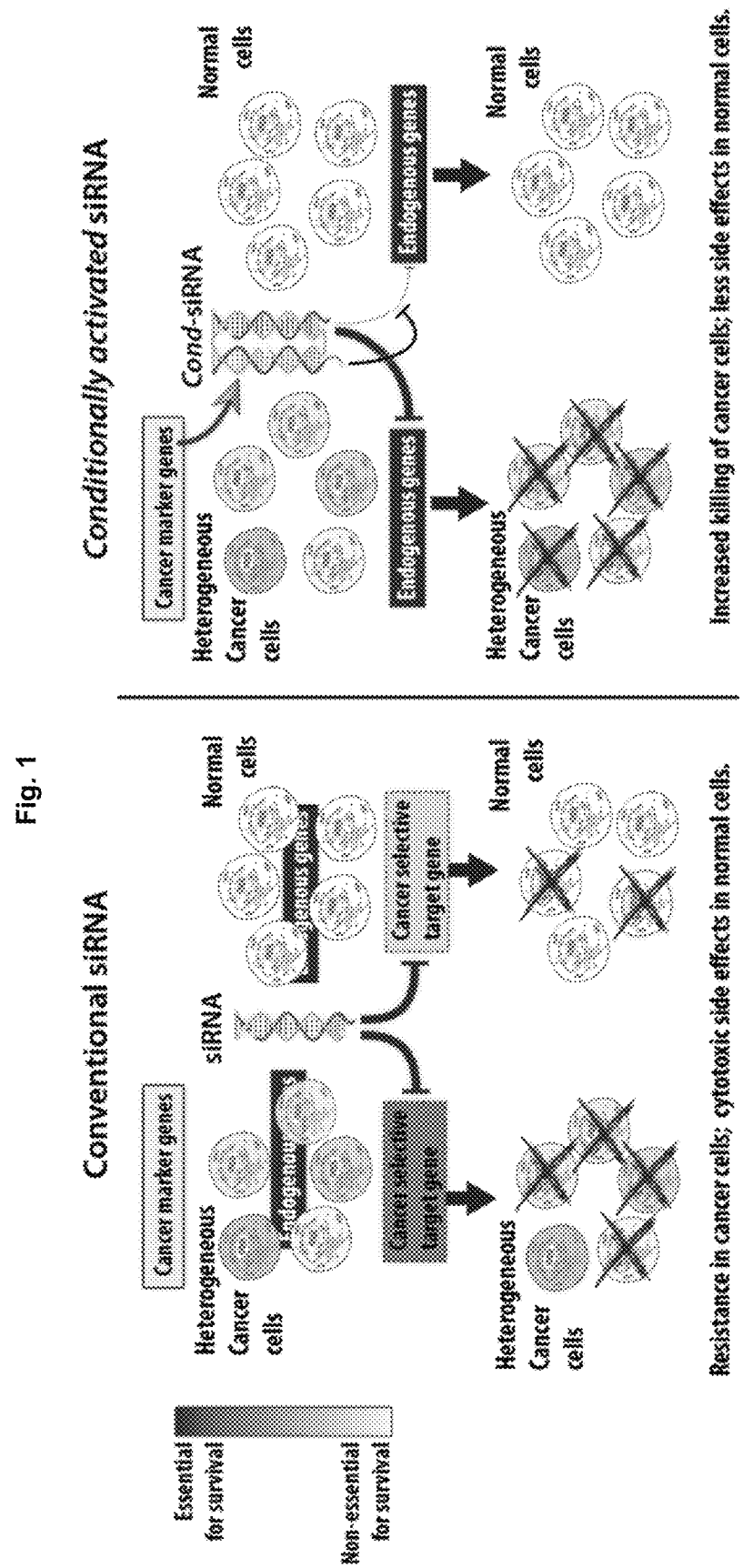
FIG. 1 shows the fundamental treatment concept for Conditionally activated-siRNAs (Cond-siRNAs).

Disclosed herein are approaches for attacking cancer cells lacking targetable survival essential mutations and resisting conventional therapies by selectively killing these cells using the RNA transcripts of mutated cancer genes to activate Cond-siRNAs targeting critical survival genes shared by cancer cells and normal cells. FIG. 1 shows the fundamental treatment concept for Cond-siRNAs and the use thereof for treating AML by killing AML cells using cell selective knock down of endogenous genes in cells that express AML associated oncogenes.

Figure 2A:
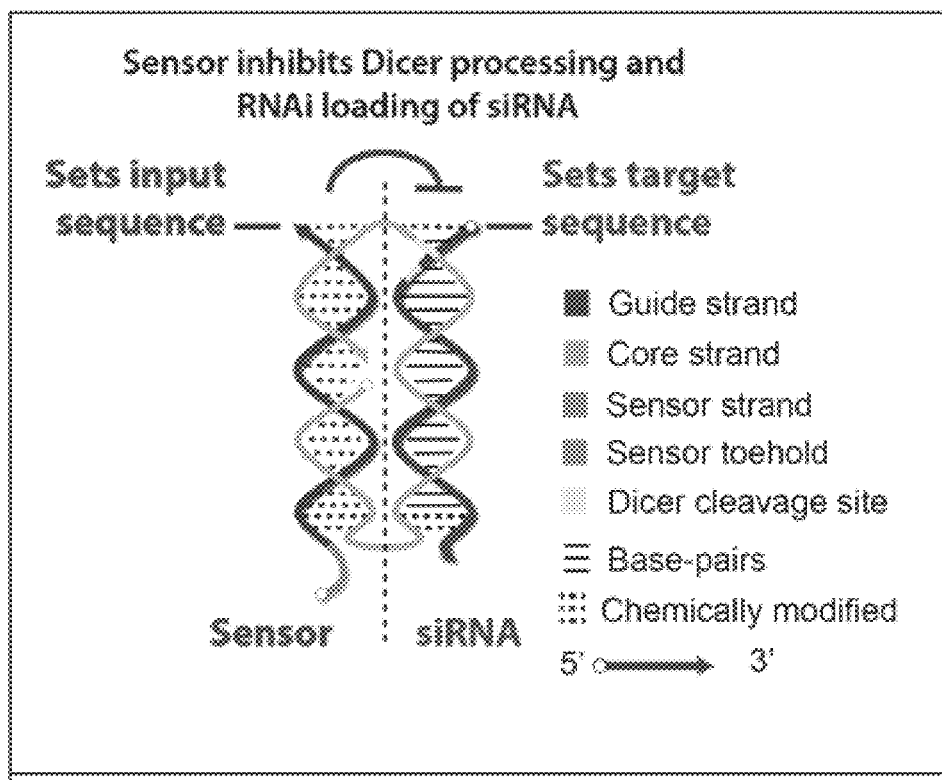
FIG. 2A shows an example of a basic design of Cond-siRNAs.
Figure 2B:
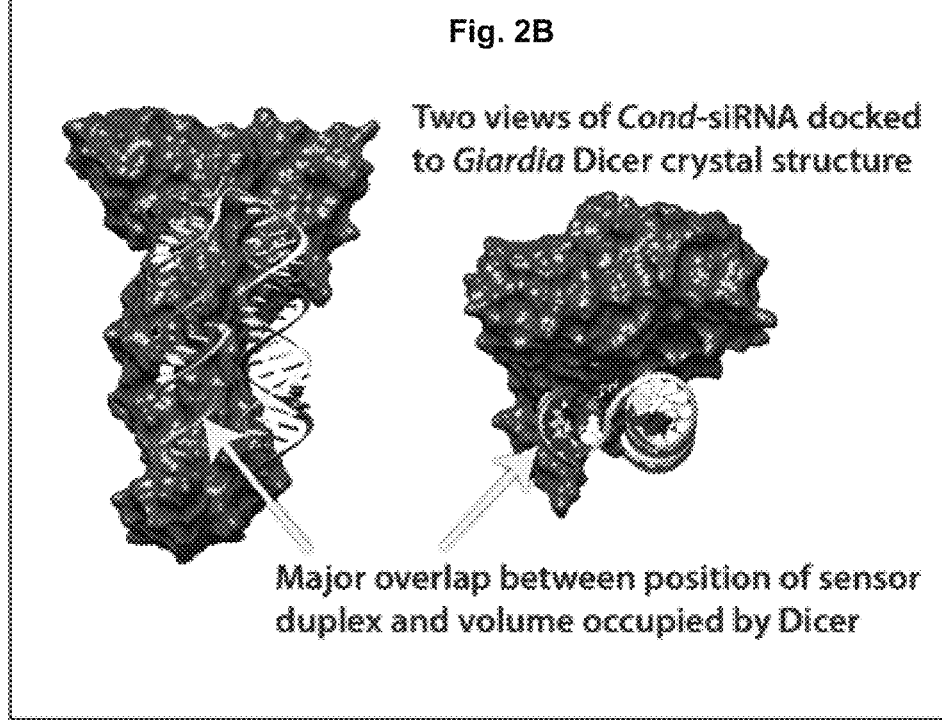
FIG. 2B illustrates how sensor duplexes block Dicer binding.

In one aspect, this disclosure relates to Cond-siRNAs that treat AML by inhibiting essential endogenous genes that express AML related fusion oncogenes. The construction and use of conditional-siRNAs programmable for activation by oncogenic transcription factors are shown in FIGS. 2A and 2B. Further details about the make and use of such constructs can be found in U.S. Pat. No. 9,725,715, entitled "Signal activatable constructs and related components compositions methods and systems," the content of which is incorporated herein by reference in its entirety. In a related aspect, pharmaceutical compositions comprising such Cond-siRNAs and one or more pharmaceutically acceptable carrier or excipient are also disclosed herein. In another related aspect, disclosed are methods of treating AML in a subject comprising administering to the subject a therapeutically effective amount of the pharmaceutical composition comprising one or more Cond-siRNAs that detect CBFβ-MYH11 gene. In some embodiments, the Cond-siRNAs target and/or inhibit MCL-1. In some embodiments, the Cond-siRNAs target and/or inhibit HDAC8.

Figure 3:
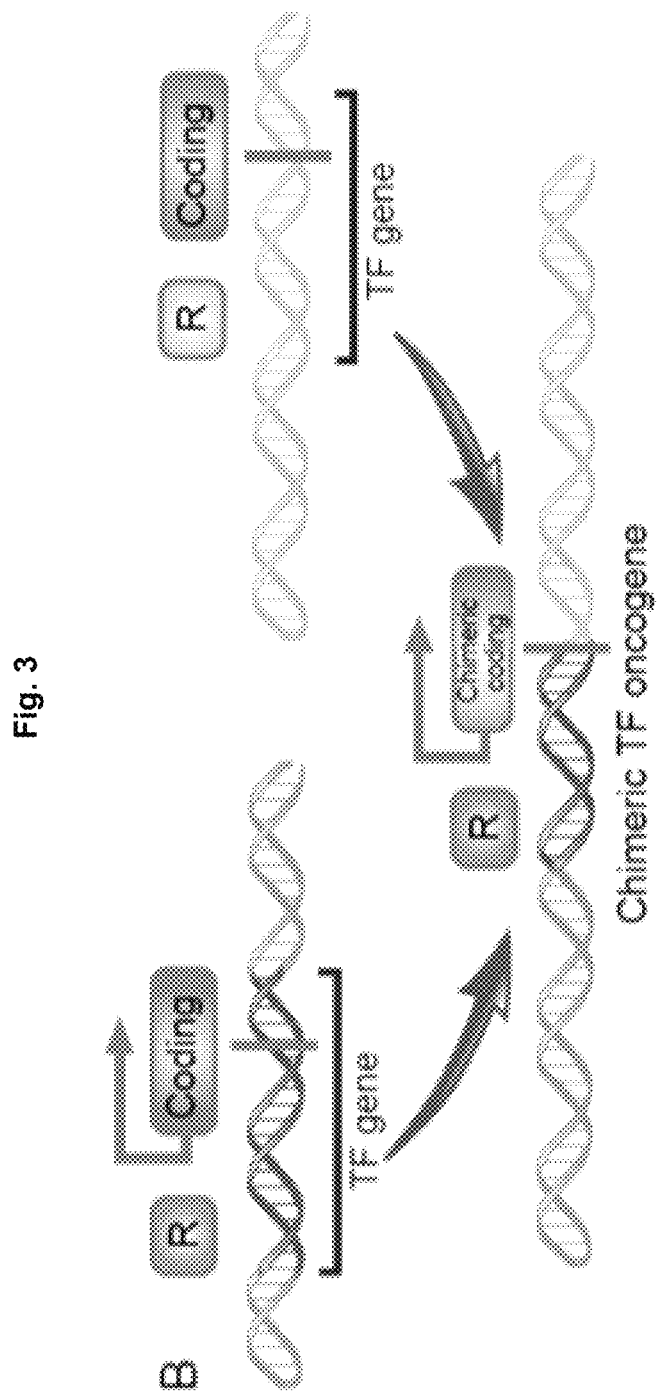
FIG. 3 illustrates the structure of fusion oncogenes (from reference 5).

In some embodiments, this disclosure relates to treating a subset of AML in which the fusion oncogene CBFβ-MYH11 was present. This chromosomal mutation is responsible for leukemogenesis and found in approximately 12% of AML patients.[5] This gene is created by a chromosome rearrangement that fuses the human CBFβ messenger RNA (mRNA) with the MYH11 mRNA (as shown in FIG. 3) at a specific point that is conserved across AML patients. While this mRNA is specifically expressed in AML cells, it is not essential for cancer cell survival. In some embodiments, the Cond-siRNAs can be activated by RNA transcripts from the CBFβ-MYH11 gene. To kill cancer cells, the Cond-siRNAs target HDAC8 or MCL-1. More detailed description can be found in Appendices B and C submitted herein, which are also included as part of this disclosure. For greater clarity, panels of Appendix A are shown in FIGS. 6-20.

Using conditional siRNA nanotechnology, an RNA nanostructure was constructed to recognize a specific sequence of the CBFβ-MYH11 gene, and to release an siRNA coding for the knockdown of MCL-1 mRNA. MCL-1 is an anti-apoptotic protein, necessary for the survival of hematopoietic stem cells and is essential for development and sustained growth of AML cells.[6] MCL-1 is an endogenous apoptosis inhibitor that is vital to the survival of hematopoietic stem cells and the maintenance of bone marrow.[7] Because of the importance of MCL-1 expression for AML cell survival, it is believed that knocking down MCL-1 mRNA in CBFβ-MYH11 AML cells will cause cancer cell death. In other embodiments, the Cond-siRNAs disclosed herein target HDAC8 to kill the cancer cells. The HDAC8 gene is a histone deacetylase that regulates transcription[8]. Inhibition of HDAC8 selectively kills AML cells[9].

Examples of Cond-siRNAs that detect CBFβ-MYH11 and inhibit either MCL-1 or HDAC8 have been developed and shown Appendices C and D.

In certain embodiments, the Cond-siRNAs complex may comprise a combination of the sensor strand, the core strand, and/or a guide strand selected from Table 1 below.

TABLE 1

| SEQ ID NOs. | STRAND | TARGET OR BIOMARKER | SEQUENCE |
|---|---|---|---|
| 1 | SENSOR | CBFb-MYH11 | 5' GACUCUCCAGCUCAUGGACCTC CAUUUCCT 3' |
| 2 | GUIDE | MCL-1 | 5' GTCUUCUGCUAAUGGUUCGAU GCUU 3' |
| 3 | GUIDE | HDAC8 | ACACTTTCACAGATCTGGT |
| 4 | CORE | MCL-1 | 5' GCUGGAGAAGUC linker |
| 5 | | | GCAUCGAACCAUUAGCAGAAGAC linker |
| 6 | | | GAGGUCCAUGA 3' |

In another embodiment, the Cond-siRNAs complex may comprise a construct that includes a sensor strand corresponding to SEQ ID NO: 1, a Guide strand corresponding to SEQ ID NO:2, and a core strand corresponding to SEQ ID NO:3.

Methods of Treatment

The cond-siRNA complexes described above may be used in methods to treat AML. In other embodiments, a method for treating AML is disclosed herein, wherein the method includes a step of administering to a subject a therapeutically effective amount of one or more of the AML related cond-siRNAs described above. As disclosed herein, the subject may be any human or other animal suffering from AML.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

The methods for treating AML include administering a therapeutically effective amount of a therapeutic composition. An "effective amount," "therapeutically effective amount" or "effective dose" is an amount of a composition (e.g., a therapeutic composition or agent) that produces a desired therapeutic effect in a subject, such as preventing or treating a target condition or alleviating symptoms associated with the condition. The precise therapeutically effective amount is an amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21st Edition, Univ. of Sciences in Philadelphia (USIP), Lippincott Williams & Wilkins, Philadelphia, Pa., 2005.

In some embodiments, one or more cond-siRNAs may be used alone or as part of a pharmaceutical composition for treating AML. Thus, in some embodiments, a pharmaceutical composition comprising any one or more of the cardiac hypertrophy-related Cond-siRNAs described above is disclosed. In some embodiments, a pharmaceutical composition comprising any one or more of the AML-related Cond-siRNAs described above is disclosed. The therapeutic compositions may also include one or more pharmaceutically acceptable carriers. A "pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

The therapeutic compositions described herein may be administered by any suitable route of administration. A route of administration may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal.

Having described the invention with reference to the embodiments and illustrative examples, those in the art may appreciate modifications to the invention as described and illustrated that do not depart from the spirit and scope of the invention as disclosed in the specification. The examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein. All appendices A-D submitted herewith constitute part of the complete disclosure.

EXAMPLES

Example 1: Design of Cond-siRNAs to Treat AMP

Figure 4:
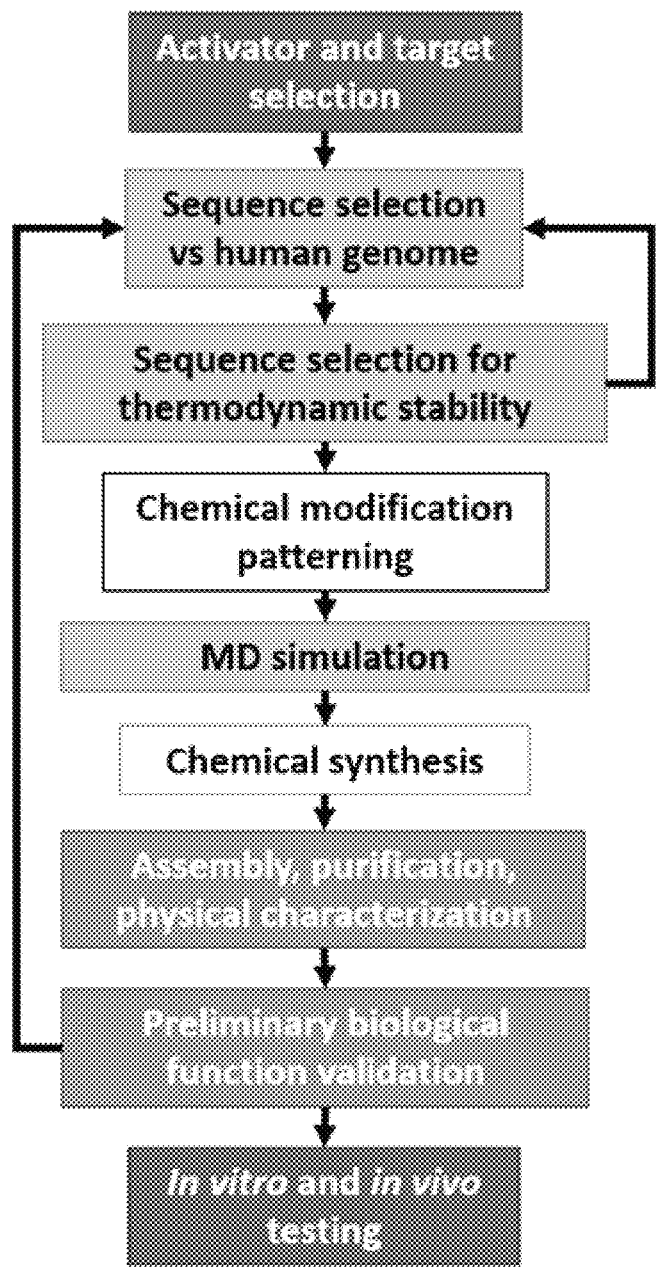
FIG. 4 shows the design and preliminary testing process for Cond-siRNAs.
Figure 5:
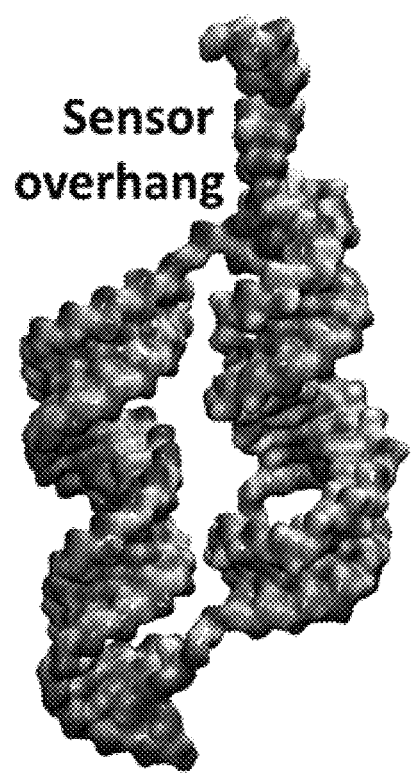
FIG. 5 shows an example of a computed model of Cond-siRNA via molecular dynamics simulation.
Figure 7:
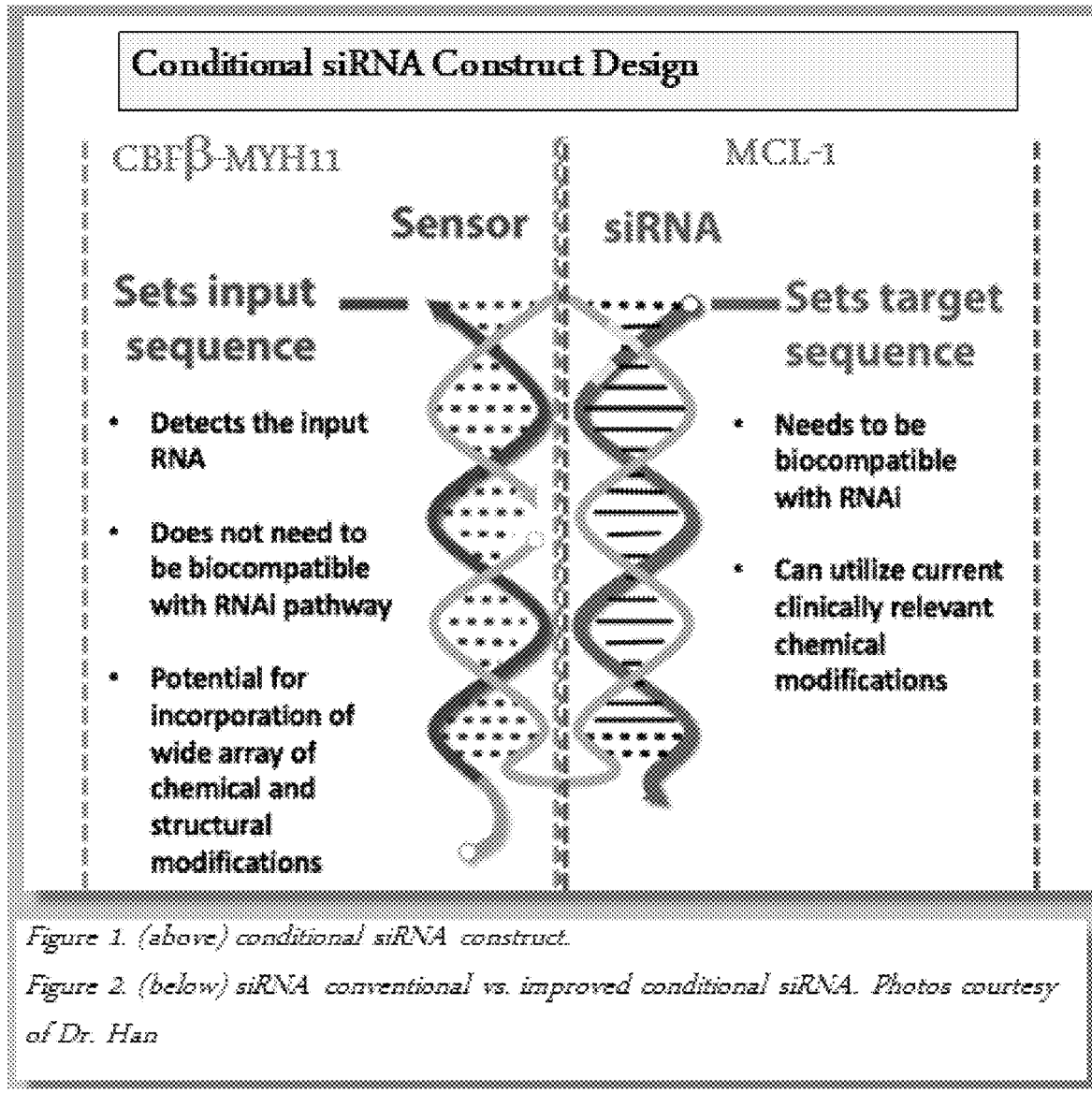
Figure 8:
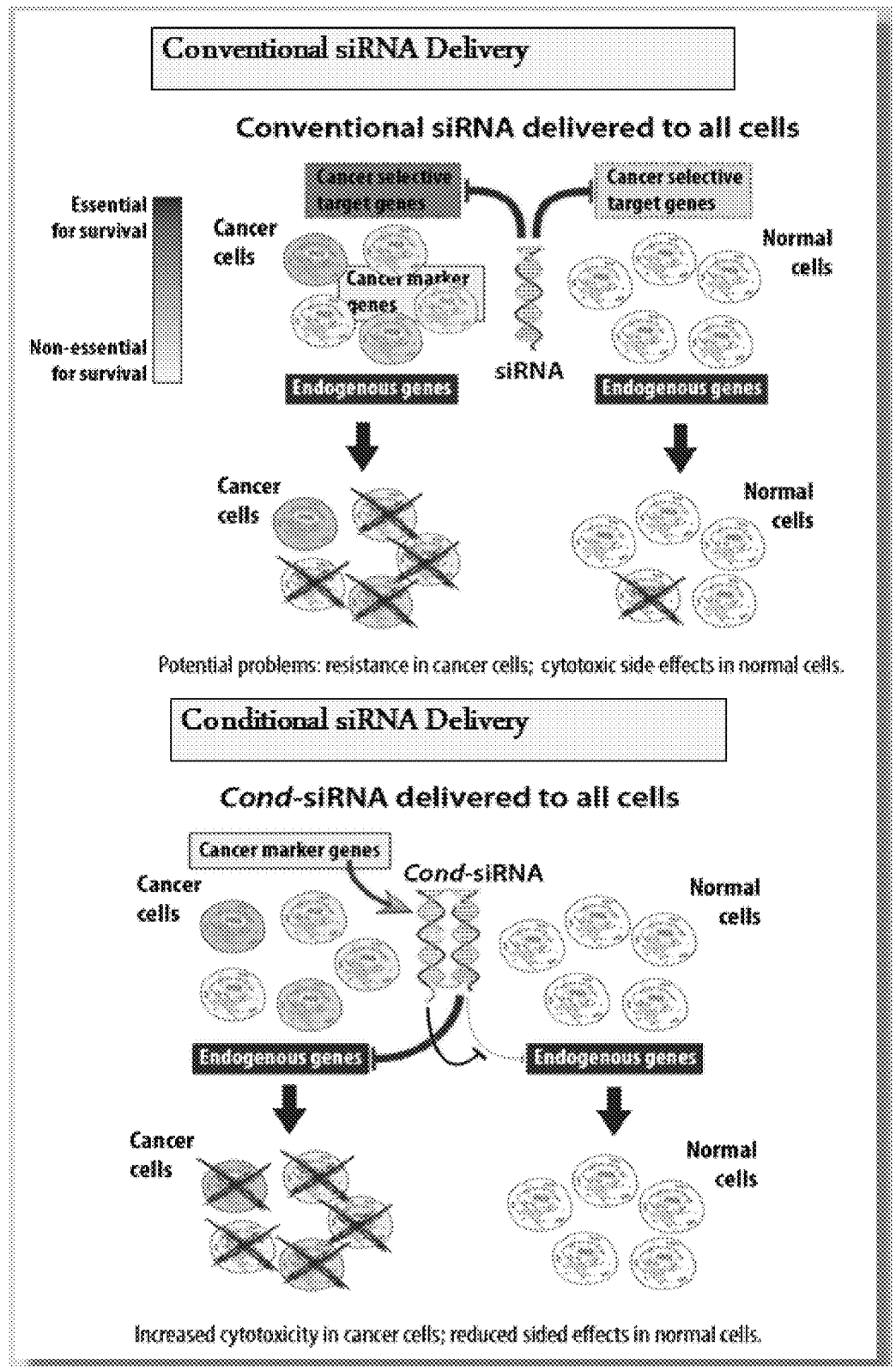

To design Cond-siRNAs for fusion oncogene activated knockdown of endogenous targets, a process of iterative design, testing and refinement as illustrated in FIG. 4 was followed. In this process, the activator (CBFβ-MYH11) and target (MCL-1) was selected in accordance with current knowledge on disease pathways. Then sensor and siRNA sequences were selected based on uniqueness in the human genome and thermodynamic stability of the resulting construct. Patterns of chemical modifications that support optimal functioning were used. Optionally, computational simulations were conducted to visualize the molecular conformation as illustrated in FIG. 5. Constructs with acceptable predicted conformations were sent for chemical synthesis by commercial vendors. Assembly and characterization of the Cond-siRNA were performed, followed by initial testing on HCT116 cells according to validated procedures. Construct design can then refined or pass on to disease model testing, depending on results.

Example 2: Design of Cond-siRNAs that Target MCL-1 and Activated by CBFβ-MYH11

The following experiment was conducted as follows: First, the Guide, Core and Sensor RNA strands are designed as follows:
MCL-1 guide strand. A Cond-siRNA complex was designed to include a sensor strand that includes the following sequence: GA+CU+TC+TCCAG+C UC+AUGGA+ CC+TC C+AUUU+C+C+T (SEQ ID NO:7). Chemical modifications can be made to the sensor strand, resulting in the following sensor strand sequence: /5Sp9/m G*mA*+ C*mU*+T*mC*+T*mC*mC*mA*mG*+C*mU*mC*+ A*mU*mG*mG*mA*+C*mC*+T*mC*mC*+ A*mU*mU*mU*+C*+C*+T*/3AmMO/ (SEQ ID NO:8)

Guide and Core Strands. The Cond-siRNA complex also includes a guide and core strand that are designed as follows:

The sequence of MCL-1 is found in Zhang et al, Oncogene (2011) 30, 1963-1968; doi:10.1038/onc.2010.559, then the CDS targeted siRNA was used to determine the MCL-1 target region—sense side, 2 different variants of MCL-1 human mRNA; sense side sequence below:

Aagct gcatcgaaccattagcaga aagtatcacaga c (SEQ ID NO:9)

Aagct gcatcgaaccattagcaga aagtat cacagac gttc (SEQ ID NO:10)

The guide strand exiqon, sequence is: /5AmMC6/+g+t c u u c u g c u a a u g g u u c g a u g C u u (SEQ ID NO:11)

And the core strand is designed as follows: G*C*U*GGAGAAGUC C3 *mG*mC*mAucgaaccauuagcaga aga*mc c3 GAGGUCCA*U*G*A (SEQ ID NO:12)

Sequences were checked by hand. The nucleotides and modifications are inducted as follows: (1)+A, +T, +C, +G are LNA; (2) mA, mU, mC, mG are 2'-O-methyl; (3) rA, rU, rC, rG are RNA; (3) * denotes phosphorothioate backbone connection; (4) /5Sp9/is a tri-ethylene glycol linker; (5) /iSpC3/ is an internal C3 spacer; (6) /5AmMC6/ is a 5' primary amine modification on a C6 linker; (7) /3AmMO/ is a 3' primary amine modification.

The sensor sequence. The sensor sequence was designed to detect fusion oncogene CBFβ-MYH11, which is a fusion oncogene seen in 12% of AML cases.

The CBFβ-MYH11 sensor strand from prototype construct (SEQ ID NO: 13)
UCGGGAGGAAAUGGAGGUCCAUGAGCUGGAGAAGUCCAAGCGGGCCCUG

GAGACCCAGAUCGGGAGGAAAUGGAGGUCCAUGAGCUGGAGAAGUC

CBFb is bolded, MYH11 is italicized, and the toehold binding region underlined.

The MCL-1 siRNA target region from literature (Zhang et al, Oncogene (2011) 30, 1963-1968; doi:10.1038/onc.2010.559), corresponding to the MCL-1 target region in CDS of MCL-1 mRNA: Aagct gcatcgaaccattagcaga aagtatcacaga c (SEQ ID NO:9)

The Cond-siRNA complex is shown in Slide 9 of Appendix B.

The constructs are annealed and then gel purified, using electro-dialysis and subsequently quantified. FIG. 14.

Then, dual luciferase experiments were carried out for ON/OFF and activation. Experimental results are shown in FIGS. 15-20 and Appendix A.

The OFF and preactivated ON cond-siRNAs constructs demonstrate a large differential target knockdown (up to ~20 fold at 1 nM) in our assays, providing a broad assay range that facilitates observation of activation.

In these experiments, a consistent two-fold activation was observed at 48 and 68 hours for the 1 nM concentration. Previous studies with similar constructs suggest that activation can be more readily observed by reducing background RNAi activity of the OFF constructs with more stringent purification and extending the time of activation.

Example 3: Testing in AML Cells

For testing on AML cell lines, Cond-siRNAs were delivered to mixed populations of AML/non-AML hematopoietic cells in suspension via lipid or (alternatively) electroporation based protocols. RNAi knockdown and selective cell killing are be measured and compared by Fluorescence Activated Cell Sorting (FACS), dual luciferase assays, Northern blots, Western blots and RT-PCR. See Appendix B, slide 12. Non-specific toxicity is measured by commercial assays for immune activation. Construct design is evolved iteratively until objectives outlined for phase one are achieved.

Treatment strategies using the complex described herein includes delivery of Cond-siRNAs broadly to myeloid cells, where they will enter AML blasts and stem cells to detect expression of CBFβ-MYH11 and consequently activate RNAi silencing of MCL-1. The leukemia blasts and stem cells would then be depleted by apoptosis. IN another alternative, Cond-siRNA against BCL-2 may be co-delivered to prevent resistance by compensatory expression of BCL-2. Other delivery strategies are shown in Slide 19 of Appendix A.

This strategy may also be viable for HIV to detect tat/rev HIV mRNA transcripts, and then inhibit MCL-1 to deplete the infected cells.

REFERENCES

1. "What are the key statistics about acute myeloid leukemia" American Cancer Society, 5 Jan. 2017, https://www.cancer.org/cancer/acute-myeloid-leukemia/about/key-statistics.html. Accessed 24 Jul. 2017.
2. Look, Thomas A. "Oncogenic Transcription Factors in the Human Acute Leukemias" Science, Vol. 278, Issue 5340, pp. 1059-1064
3. Glaser, Stefan P. et al. "Anti-apoptotic Mcl-1 is essential for the development and sustained growth of acute myeloid leukemia" Genes & Dev, Vol. 26 pp. 120-125

What is claimed is:

1. A conditional RNA-sensor complex comprising:
   a sensor strand comprising at least one toehold segment, wherein the toehold segment binds a pathological biomarker associated with acute myeloid leukemia (AML); and
   a double stranded pro-RNA molecule comprising
   a guide strand comprising an RNA molecule that binds a therapeutic target molecule; and
   a core strand comprising
   a first portion comprising a passenger strand that is fully or partially complimentary to and binds the guide strand;
   a second portion comprising a first protection segment that is fully or partially complimentary to and binds the sensor strand; and
   a first linker that joins a first end of the passenger strand to the first protection segment,
   wherein the sensor strand comprises a sequence having at least 95% homology to SEQ ID NO:1, and
   wherein the double stranded pro-RNA molecule is an RNA interference (RNAi) molecule and the therapeutic target molecule is MCL-1 or HDAC8.

2. The conditional RNA-sensor complex of claim 1, wherein the core strand further comprises a third portion comprising a second protection segment that is fully or partially complimentary to and binds the sensor strand, and a second linker that joins a second end of the passenger strand to the second protection segment.

3. The conditional RNA-sensor complex of claim 1, wherein the toehold segment is an aptamer.

4. The conditional RNA-sensor complex of claim 1, wherein the sensor strand is displaced from the double stranded pro-RNA molecule when the pathological biomarker binds the toehold segment and the resulting double stranded pro-RNA molecule is a substrate for Dicer.

5. The conditional RNA-sensor complex of claim 1, wherein the pathological biomarker comprises a molecule that encodes a portion of CBFβ-MYH11.

6. The conditional RNA-sensor complex of claim 1, wherein the sensor strand comprises SEQ ID NO:1.

7. The conditional RNA-sensor complex of claim 1, wherein the guide strand comprises SEQ ID NO:2 or SEQ ID NO:3.

8. The conditional RNA-sensor complex of claim 2, wherein the core strand comprises
   a passenger strand;
   a first linker that joins a 3' end of the passenger strand to the first protection segment; and
   a second linker that joins a 5' end of the passenger strand to the second protection segment.

9. The conditional RNA-sensor complex of claim 8, wherein the core strand comprises SEQ ID NOs:4, 5 or 6.

10. The conditional RNA-sensor complex of claim 6, wherein the sensor strand, the guide strand and/or the core strand further comprises one or more chemical modifications to the RNA sequence, wherein the one or more chemical modifications are selected from a locked nucleic acid (LNA) modification, a peptide nucleic acid (PNA) modification, a 2'-O-methyl modification, morpholino modification, a phosphorothioate modification, a terminal modification, or a linker modification.

11. The conditional RNA-sensor complex of claim 10, wherein the sensor strand comprises SEQ ID NO:7.

12. The conditional RNA-sensor complex of claim 10, wherein the sensor strand comprises SEQ ID NO:8.

13. The conditional RNA-sensor complex of claim 1, wherein the core strand comprises a sequence having at least 95% homology to SEQ ID NOs:4, 5 or 6, and the guide strand comprises a sequence having at least 95% homology to SEQ ID NO:2.

14. The conditional RNA-sensor complex of claim 13, wherein the sensor strand, the guide strand and/or the core strand further comprises one or more chemical modifications to the RNA sequence, wherein the one or more chemical modifications are selected from a locked nucleic acid (LNA) modification, a peptide nucleic acid (PNA) modification, a 2'-O-methyl modification, morpholino modification, a phosphorothioate modification, a terminal modification, or a linker modification.

15. A pharmaceutical composition comprising:
   a conditional RNA-sensor complex of claim 1; and
   a pharmaceutically acceptable carrier or excipient.

16. A method of treating acute myeloid leukemia (AML) comprising administering a therapeutically effective amount of a conditional RNA-sensor complex of claim 1 to a subject suffering from AML.

\* \* \* \* \*

SEQUENCE LISTING

```
<160> NUMBER OF SEQ ID NOS: 29

<210> SEQ ID NO 1
<211> LENGTH: 31
<212> TYPE: DNA
<213> ORGANISM: Artificial Sequence
<220> FEATURE:
<223> OTHER INFORMATION: sensor strand

<400> SEQUENCE: 1
gacutctcca gcucauggac ctccauuucc t                          31

<210> SEQ ID NO 2
<211> LENGTH: 25
<212> TYPE: DNA
<213> ORGANISM: Artificial Sequence
<220> FEATURE:
<223> OTHER INFORMATION: guide strand

<400> SEQUENCE: 2
gtcuucugcu aaugguucga ugcuu                                 25

<210> SEQ ID NO 3
<211> LENGTH: 19
<212> TYPE: DNA
<213> ORGANISM: Artificial Sequence
<220> FEATURE:
<223> OTHER INFORMATION: guide strand

<400> SEQUENCE: 3
acactttcac agatctggt                                        19

<210> SEQ ID NO 4
<211> LENGTH: 12
<212> TYPE: RNA
<213> ORGANISM: Artificial Sequence
<220> FEATURE:
<223> OTHER INFORMATION: core strand

<400> SEQUENCE: 4
gcuggagaag uc                                               12

<210> SEQ ID NO 5
<211> LENGTH: 23
<212> TYPE: RNA
<213> ORGANISM: Artificial Sequence
<220> FEATURE:
<223> OTHER INFORMATION: core strand
```

<400> SEQUENCE: 5
gcaucgaacc auuagcagaa gac                                           23

<210> SEQ ID NO 6
<211> LENGTH: 11
<212> TYPE: RNA
<213> ORGANISM: Artificial Sequence
<220> FEATURE:
<223> OTHER INFORMATION: core strand

<400> SEQUENCE: 6
gagguccaug a                                                        11

<210> SEQ ID NO 7
<211> LENGTH: 31
<212> TYPE: DNA
<213> ORGANISM: Artificial Sequence
<220> FEATURE:
<223> OTHER INFORMATION: CBFbeta-MYH11 sensor
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (5)..(5)
<223> OTHER INFORMATION: LNA
<220> FEATURE:
<221> NAME/KEY: misc_feature
<222> LOCATION: (7)..(7)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (15)..(15)
<223> OTHER INFORMATION: LNA
<220> FEATURE:
<221> NAME/KEY: misc_feature
<222> LOCATION: (20)..(20)
<223> OTHER INFORMATION: LNA
<220> FEATURE:
<221> NAME/KEY: misc_feature
<222> LOCATION: (22)..(22)
<223> OTHER INFORMATION: LNA
<220> FEATURE:
<221> NAME/KEY: misc_feature
<222> LOCATION: (25)..(25)
<223> OTHER INFORMATION: LNA
<220> FEATURE:
<221> NAME/KEY: misc_feature
<222> LOCATION: (29)..(31)
<223> OTHER INFORMATION: LNA

<400> SEQUENCE: 7
gacutctcca gcucauggac ctccauuucc t                                  31

<210> SEQ ID NO 8
<211> LENGTH: 31
<212> TYPE: DNA
<213> ORGANISM: Artificial Sequence
<220> FEATURE:
<223> OTHER INFORMATION: Y3 sensor
<220> FEATURE:
<221> NAME/KEY: misc_feature
<222> LOCATION: (1)..(31)
<223> OTHER INFORMATION: phosphorothioate backbone connection
<220> FEATURE:
<221> NAME/KEY: misc_feature
<222> LOCATION: (1)..(2)

```
<223> OTHER INFORMATION: 2'-O-methyl
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: LNA
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: LNA
<220> FEATURE:
<221> NAME/KEY: misc_feature
<222> LOCATION: (8)..(11)
<223> OTHER INFORMATION: 2'-O-methyl
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (13)..(14)
<223> OTHER INFORMATION: 2'-O-methyl
<220> FEATURE:
<221> NAME/KEY: misc_feature
<222> LOCATION: (15)..(15)
<223> OTHER INFORMATION: LNA
<220> FEATURE:
<221> NAME/KEY: misc_feature
<222> LOCATION: (16)..(19)
<223> OTHER INFORMATION: 2'-O-methyl
<220> FEATURE:
<221> NAME/KEY: misc_feature
<222> LOCATION: (20)..(20)
<223> OTHER INFORMATION: LNA
<220> FEATURE:
<221> NAME/KEY: misc_feature
<222> LOCATION: (21)..(21)
<223> OTHER INFORMATION: 2'-O-methyl
<220> FEATURE:
<221> NAME/KEY: misc_feature
<222> LOCATION: (22)..(22)
<223> OTHER INFORMATION: LNA
<220> FEATURE:
<221> NAME/KEY: misc_feature
<222> LOCATION: (23)..(24)
<223> OTHER INFORMATION: 2'-O-methyl
<220> FEATURE:
<221> NAME/KEY: misc_feature
<222> LOCATION: (25)..(25)
<223> OTHER INFORMATION: LNA
<220> FEATURE:
<221> NAME/KEY: misc_feature
<222> LOCATION: (26)..(28)
<223> OTHER INFORMATION: 2'-O-methyl
<220> FEATURE:
<221> NAME/KEY: misc_feature
<222> LOCATION: (30)..(31)
<223> OTHER INFORMATION: LNA

<400> SEQUENCE: 8
gacutctcca gcucauggac ctccauuucc t                                    31

<210> SEQ ID NO 9
<211> LENGTH: 37
<212> TYPE: DNA
<213> ORGANISM: Homo sapiens
```

<400> SEQUENCE: 9
aagctgcatc gaaccattag cagaaagtat cacagac                                     37

<210> SEQ ID NO 10
<211> LENGTH: 41
<212> TYPE: DNA
<213> ORGANISM: Homo sapiens

<400> SEQUENCE: 10
aagctgcatc gaaccattag cagaaagtat cacagacgtt c                                41

<210> SEQ ID NO 11
<211> LENGTH: 25
<212> TYPE: DNA
<213> ORGANISM: Artificial Sequence
<220> FEATURE:
<223> OTHER INFORMATION: guide strand
<220> FEATURE:
<221> NAME/KEY: misc_feature
<222> LOCATION: (1)..(2)
<223> OTHER INFORMATION: LNA

<400> SEQUENCE: 11
gtcuucugcu aaugguucga ugcuu                                                  25

<210> SEQ ID NO 12
<211> LENGTH: 48
<212> TYPE: RNA
<213> ORGANISM: Artificial Sequence
<220> FEATURE:
<223> OTHER INFORMATION: core strand
<220> FEATURE:
<221> NAME/KEY: misc_feature
<222> LOCATION: (1)..(3)
<223> OTHER INFORMATION: phosphorothioate backbone connection
<220> FEATURE:
<221> NAME/KEY: misc_feature
<222> LOCATION: (13)..(15)
<223> OTHER INFORMATION: phosphorothioate backbone connection
<220> FEATURE:
<221> NAME/KEY: misc_feature
<222> LOCATION: (14)..(16)
<223> OTHER INFORMATION: 2'-O-methyl
<220> FEATURE:
<221> NAME/KEY: misc_feature
<222> LOCATION: (35)..(35)
<223> OTHER INFORMATION: phosphorothioate backbone connection
<220> FEATURE:
<221> NAME/KEY: misc_feature
<222> LOCATION: (36)..(36)
<223> OTHER INFORMATION: 2'-O-methyl
<220> FEATURE:
<221> NAME/KEY: misc_feature
<222> LOCATION: (45)..(47)
<223> OTHER INFORMATION: phosphorothioate backbone connection

<400> SEQUENCE: 12
gcuggagaag uccgcaucga accauuagca gaagaccgag guccauga                         48

<210> SEQ ID NO 13
<211> LENGTH: 95
<212> TYPE: RNA
<213> ORGANISM: Artificial Sequence
<220> FEATURE:
<223> OTHER INFORMATION: CBFbeta-MYH11 sensor strand
<220> FEATURE:
<221> NAME/KEY: misc_feature
<222> LOCATION: (65)..(76)
<223> OTHER INFORMATION: CBFbeta
<220> FEATURE:

```
<221> NAME/KEY: misc_feature
<222> LOCATION: (65)..(72)
<223> OTHER INFORMATION: toehold binding region
<220> FEATURE:
<221> NAME/KEY: misc_feature
<222> LOCATION: (77)..(95)
<223> OTHER INFORMATION: MYH11

<400> SEQUENCE: 13
ucgggaggaa auggaggucc augagcugga gaaguccaag cgggcccugg agacccagau    60
cgggaggaaa uggaggucca ugagcuggag aaguc                              95

<210> SEQ ID NO 14
<211> LENGTH: 62
<212> TYPE: DNA
<213> ORGANISM: Homo sapiens

<400> SEQUENCE: 14
aggaaatgga ggtccatgag ctggagaagt caggaaatgg aggtccatga gctggagaag    60
tc                                                                  62

<210> SEQ ID NO 15
<211> LENGTH: 31
<212> TYPE: RNA
<213> ORGANISM: Artificial Sequence
<220> FEATURE:
<223> OTHER INFORMATION: MFE structure

<400> SEQUENCE: 15
gacuucucca gcucauggac cuccauuucc u                                  31

<210> SEQ ID NO 16
<211> LENGTH: 10
<212> TYPE: DNA
<213> ORGANISM: Artificial Sequence
<220> FEATURE:
<223> OTHER INFORMATION: Y3 sensor

<400> SEQUENCE: 16
ggaccccagg                                                          10

<210> SEQ ID NO 17
<211> LENGTH: 25
<212> TYPE: RNA
<213> ORGANISM: Artificial Sequence
<220> FEATURE:
<223> OTHER INFORMATION: guide strand

<400> SEQUENCE: 17 gcuucugcu aaugguucga ugcuu                                          25

<210> SEQ ID NO 18
<211> LENGTH: 25
<212> TYPE: DNA
<213> ORGANISM: Homo sapiens

<400> SEQUENCE: 18
cgucacactt tcacagatct ggtaa                                         25

<210> SEQ ID NO 19
<211> LENGTH: 59
<212> TYPE: RNA
<213> ORGANISM: Homo sapiens

<400> SEQUENCE: 19
```
ucgggaggaa auggaggucc augagcugga gaaguccaag cgggcccugg agacccaga       59

<210> SEQ ID NO 20
<211> LENGTH: 20
<212> TYPE: DNA
<213> ORGANISM: Homo sapiens

<400> SEQUENCE: 20
atggaggtcc atgagctgga       20

<210> SEQ ID NO 21
<211> LENGTH: 20
<212> TYPE: DNA
<213> ORGANISM: Homo sapiens

<400> SEQUENCE: 21
atggaggtcc gtgagctgga       20

<210> SEQ ID NO 22
<211> LENGTH: 15
<212> TYPE: DNA
<213> ORGANISM: Homo sapiens

<400> SEQUENCE: 22
aggtccatga gctgg       15

<210> SEQ ID NO 23
<211> LENGTH: 48
<212> TYPE: RNA
<213> ORGANISM: Homo sapiens

<400> SEQUENCE: 23
ggagguccau gacaccagau cugugaaagu gugacgccgg gaggaaau       48

<210> SEQ ID NO 24
<211> LENGTH: 31
<212> TYPE: RNA
<213> ORGANISM: Homo sapiens

<400> SEQUENCE: 24
ucuccagcuc auggaccucc auuuccuccc g       31

<210> SEQ ID NO 25
<211> LENGTH: 31
<212> TYPE: DNA
<213> ORGANISM: Homo sapiens

<400> SEQUENCE: 25
tctccagctc auggacctcc auutccuccc g       31

<210> SEQ ID NO 26
<211> LENGTH: 17
<212> TYPE: DNA
<213> ORGANISM: Homo sapiens

<400> SEQUENCE: 26
tcgggaggaa atggagg       17

<210> SEQ ID NO 27
<211> LENGTH: 48
<212> TYPE: RNA
<213> ORGANISM: Homo sapiens

```
<400> SEQUENCE: 27
gcuggagaag uccaccagau cugugaaagu gugacgcgag guccauga        48

<210> SEQ ID NO 28
<211> LENGTH: 25
<212> TYPE: RNA
<213> ORGANISM: Homo sapiens

<400> SEQUENCE: 28
cgucauaaac acuuuaaaca cuggc                                 25

<210> SEQ ID NO 29
<211> LENGTH: 46
<212> TYPE: RNA
<213> ORGANISM: Homo sapiens

<400> SEQUENCE: 29
gcuggagaag uccaguguuu aaaguguuua ugacggaggu ccauga          46
```